US009423401B2

(12) United States Patent
Varki et al.

(10) Patent No.: US 9,423,401 B2
(45) Date of Patent: Aug. 23, 2016

(54) COMPOSITIONS AND METHODS FOR DETECTING CANCER

(71) Applicants:The Regents of the University of California, Oakland, CA (US); Sialix, Inc., Newton, MA (US)

(72) Inventors: Ajit Varki, La Jolla, CA (US); Richard B. Schwab, La Jolla, CA (US); Vered Padler-Karavani, San Diego, CA (US); Nancy Hurtado-Ziola, La Jolla, CA (US)

(73) Assignees: The Regents of the University of California, Oakland, CA (US); Siamab Therapeutics, Inc., Newton, MA (US)

( * ) Notice: Subject to any disclaimer, the term of this patent is extended or adjusted under 35 U.S.C. 154(b) by 0 days.

(21) Appl. No.: 14/138,879

(22) Filed: Dec. 23, 2013

(65) Prior Publication Data

US 2014/0113979 A1 Apr. 24, 2014

Related U.S. Application Data

(62) Division of application No. 13/007,237, filed on Jan. 14, 2011, now abandoned.

(60) Provisional application No. 61/295,386, filed on Jan. 15, 2010.

(51) Int. Cl.
*G01N 33/574* (2006.01)
*C07K 16/30* (2006.01)

(52) U.S. Cl.
CPC ........ *G01N 33/5748* (2013.01); *C07K 16/3076* (2013.01); *G01N 33/57484* (2013.01); *G01N 2400/00* (2013.01)

(58) Field of Classification Search
CPC .................................................. G01N 33/574
USPC ....................................................... 435/7.23
See application file for complete search history.

(56) References Cited

U.S. PATENT DOCUMENTS

| 4,816,397 | A | 3/1989 | Boss et al. ................. 435/69.6 |
|---|---|---|---|
| 4,816,567 | A | 3/1989 | Cabilly et al. ............. 530/387.3 |
| 4,975,369 | A | 12/1990 | Beavers et al. ............. 435/69.1 |
| 4,978,745 | A | 12/1990 | Schoemaker et al. ..... 530/387.3 |
| 5,902,725 | A | 5/1999 | Robbins et al. ............... 435/7.1 |
| 2007/0059769 | A1 | 3/2007 | Blixt et al. ..................... 435/7.1 |
| 2007/0275409 | A1 | 11/2007 | Varki et al. .................... 435/7.1 |
| 2008/0019968 | A1* | 1/2008 | Blixt et al. ................. 424/138.1 |
| 2010/0075344 | A1 | 3/2010 | Vuskovic et al. ............ 435/7.23 |

FOREIGN PATENT DOCUMENTS

| WO | WO 2005/010485 | 2/2005 |
|---|---|---|
| WO | PCT/US2005/007370 | 9/2005 |
| WO | WO/2005/088310 | 9/2005 |
| WO | WO/2011/088385 | 7/2011 |

OTHER PUBLICATIONS

U.S. Appl. No. 60/629,666, filed Nov. 19, 2004.
U.S. Appl. No. 60/833,249, Bovin, N. V., filed Jul. 26, 2006.
U.S. Appl. No. 61/295,386, Varki, A., filed Jan. 15, 2010.
Adams, G. P. et al. (2005) "Monoclonal antibody therapy of cancer," *Nature Biotechnology* 23(9), 1147-1157.
An, H. J. et al. (2009) "Glycomics and disease markers," *Current Opinion in Chemical Biology* 13(5-6), 601-607.
Andreu, P. et al. (2010) "FcRγ Activation Regulates Inflammation-Associated Squamous Carcinogenesis," *Cancer Cell* 17(2), 121-134.
Bardor, M. et al. (2005) "Mechanism of Uptake and Incorporation of the Non-human Sialic Acid N-Glycolylneuraminic Acid into Human Cells," *Journal of Biological Chemistry* 280(6), 4228-4237.
Candefjord, S. et al. (2009) "Technologies for localization and diagnosis of prostate cancer," *Journal of Medical Engineering & Technology* 33(8), 585-603.
Cao, Y. et al. (1996) "Thomsen-Friedenreich-related carbohydrate antigens in normal adult human tissues: a systematic and comparative study," *Histochemistry and Cell Biology* 106(2), 197-207.
Cavadas, V. et al. (2010) "Prostate Cancer Prevention Trial and European Randomized Study of Screening for Prostate Cancer Risk Calculators: A Performance Comparison in a Contemporary Screened Cohort," *European Urology* 58(4), 551-558.
Chun-Chi, L. et al. (2009) "Integrative disease classification based on cross-platform microarray data," *BMC Bioinformatics* 10, 1-8.
Conze, T. et al. (2010) "MUC2 mucin is a major carrier of the cancer-associated sialyl-Tn antigen in intestinal metaplasia and gastric carcinomas," *Glycobiology* 20(2), 199-206.
De León, J. et al. (2008) "Differential influence of the tumour-specific non-human sialic acid containing GM3 ganglioside on CD4+CD25—effector and naturally occurring CD4+CD25+ regulatory T cells function," *International Immunology* 20(4), 591-600.
De Visser, K. E. et al. (2005) "De novo carcinogenesis promoted by chronic inflammation is B lymphocyte dependent," *Cancer Cell* 7(5), 411-423.
Desmetz, C. et al. (2009) "Humoral response to cancer as a tool for biomarker discovery," *Journal of Proteomics* 72(6), 982-988.
Desmetz, C. et al. (2009) "Identifying autoantibody signatures in cancer: a promising challenge," *Expert Review of Proteomics* 6(4), 377-386.
Devine, P. L. et al. (1991) "The Breast Tumor-associated Epitope Defined by Monoclonal Antibody 3E1.2 Is an O-linked Mucin Carbohydrate Containing N-Glycolylneuraminic Acid," *Cancer Research* 51(21), 5826-5836.
Díaz, A. et al. (2003) "Immune responses in breast cancer patients immunized with an anti-idiotype antibody mimicking NeuGc-containing gangliosides," *Clinical Immunology* 107(2), 80-89.
Diaz, S. L. et al. (2009) "Sensitive and Specific Detection of the Non-Human Sialic Acid *N*-Glycolylneuraminic Acid in Human Tissues and Biotherapeutic Products," *PLoS ONE* 4(1), e4241.

(Continued)

*Primary Examiner* — Yan Xiao
(74) *Attorney, Agent, or Firm* — Medlen & Carroll, LLP

(57) ABSTRACT

The invention provides sialylated glycans and antibodies that specifically bind to them. The invention's compositions and methods for using them are useful for early detection and diagnosis of cancer.

13 Claims, 4 Drawing Sheets

(56) References Cited

OTHER PUBLICATIONS

Drake, P. M. et al. (2010) "Sweetening the Pot: Adding Glycosylation to the Biomarker Discovery Equation," *Clinical Chemistry* 56(2), 223-236.

Du, J. et al. (2009) "Metabolic glycoengineering: Sialic acid and beyond," *Glycobiology* 19(12), 1382-1401.

Dube, D. H. et al. (2005) "Glycans in cancer and inflammation—potential for therapeutics and diagnostics," *Nature Reviews Drug Discovery* 4(6), 477-488.

Fawcett, T. (2004) "ROC Graphs: Notes and Practical Considerations for Data Mining Researchers," *Intelligent Enterprise Technologies Laboratory*,(HP Laboratories Palo Alto), 1-27.

Ferris, R. L. et al. (2010) "Tumor Antigen—Targeted, Monoclonal Antibody—Based Immunotherapy: Clinical Response, Cellular Immunity, and Immunoescape," *Journal of Clinical Oncology* 28(28), 4390-4399.

Finn, O. J. (2008) "Cancer Immunology," *New England Journal of Medicine* 358(25), 2704-2715.

Ghaderi, D. et al. (2010) "Implications of the presence of N-glycolylneuraminic acid in recombinant therapeutic glycoproteins," *Nature Biotechnology* 28(8), 863-867.

Greene, K. L. et al. (2009) "Prostate Specific Antigen Best Practice Statement: 2009 Update," *The Journal of Urology* 182(5), 2232-2241.

Gupta, D. et al. (2009) "Role of CA125 in predicting ovarian cancer survival—a review of the epidemiological literature," *Journal of Ovarian Research* 2(1), 13.

Hara, S. et al. (1986) "Highly sensitive determination of N-acetyl- and N-glycolylneuraminic acids in human serum and urine and rat serum by reversed-phase liquid chromatography with fluorescence detection," *Journal of Chromatography A* 377,111-119.

Hawkins, D. M. (2003) "The Problem of Overfitting," *Journal of Chemical Information and Computer Sciences* 44(1), 1-12.

Hedlund, M. et al. (2008) "Evidence for a human-specific mechanism for diet and antibody-mediated inflammation in carcinoma progression," *Proceedings of the National Academy of Sciences* 105(48), 18936-18941.

Hedlund, M. et al. (2007) "N-Glycolylneuraminic Acid Deficiency in Mice: Implications for Human Biology and Evolution," *Molecular and Cellular Biology* 27(12), 4340-4346.

Imai, J. et al. (2001) "Immunohistochemical expression of T, Tn and sialyl-Tn antigens and clinical outcome in human breast carcinoma," *Anticancer Research* 21(2B), 1327-1334.

Inoue, S. et al. (2010) "Extensive enrichment of N-glycolylneuraminic acid in extracellular sialoglycoproteins abundantly synthesized and secreted by human cancer cells," *Glycobiology* 20(6), 752-762.

Johansen, E. et al. (2009) "A Lectin HPLC Method to Enrich Selectively-glycosylated Peptides from Complex Biological Samples," *Journal of Visualized Experiments*(32), 1398.

Jolles, S. et al. (2005) "Clinical uses of intravenous immunoglobulin," *Clinical & Experimental Immunology* 142(1), 1-11.

Ju, T. et al. (2002) "A unique molecular chaperone Cosmc required for activity of the mammalian core 1 β3- galactosyltransferase," *Proceedings of the National Academy of Sciences* 99(26), 16613-16618.

Ju, T. et al. (2008) "Human Tumor Antigens Tn and Sialyl Tn Arise from Mutations in Cosmc," *Cancer Research* 68(6), 1636-1646.

Kim, G. E. et al. (2002) "Aberrant expression of MUC5AC and MUC6 gastric mucins and sialyl Tn antigen in intraepithelial neoplasms of the pancreas," *Gastroenterology* 123(4), 1052-1060.

Kim, Y.-S. et al. (2009) "Implication of Aberrant Glycosylation in Cancer and Use of Lectin for Cancer Biomarker Discovery," *Protein & Peptide Letters* 16(5), 499-507.

Kim, Y. et al. (1997) "Perspectives on the significance of altered glycosylation of glycoproteins in cancer," *Glycoconjugate Journal* 14(5), 569-576.

Kjeldsen, T. et al. (1988) "Preparation and Characterization of Monoclonal Antibodies Directed to the Tumor-associated O-linked Sialosyl-2→6 α-N-Acetylgalactosaminyl (Sialosyl-Tn) Epitope," *Cancer Research* 48(8), 2214-2220.

Kobata, A. et al. (2005) "Altered glycosylation of proteins produced by malignant cells, and application for the diagnosis and immunotherapy of tumours," *Immunology & Cell Biology* 83(4), 429-439.

Kobayashi, H. et al. (1992) "Serum sialyl Tn as an independent predictor of poor prognosis in patients with epithelial ovarian cancer," *Journal of Clinical Oncology* 10(1), 95-101.

Li, C. et al. (2008) "Pancreatic Cancer Serum Detection Using a Lectin/Glyco-Antibody Array Method," *Journal of Proteome Research* 8(2), 483-492.

Ludwig, J. A. et al. (2005) "Biomarkers in Cancer Staging, Prognosis and Treatment Selection," *Nature Reviews Cancer* 5(11), 845-856.

Malykh, Y. N. et al. (2001) "N-Glycolylneuraminic acid in human tumours," *Biochimie* 83(7), 623-634.

Marcial, V. A. (1977) "Carcinoma of the cervix. Present status and future," *Cancer* 39(Supplement S2), 945-958.

Martin, L. T. et al. (2002) "Genetically Altered Mice with Different Sialyltransferase Deficiencies Show Tissue-specific Alterations in Sialylation and Sialic Acid 9-O-Acetylation," *Journal of Biological Chemistry* 277(36), 32930-32938.

Mechref, Y. et al. (2009) "Quantitative Serum Glycomics of Esophageal Adenocarcinoma and Other Esophageal Disease Onsets," *Journal of Proteome Research* 8(6), 2656-2666.

Nelson, A. E. et al. (2009) "Population screening and early detection of ovarian cancer in asymptomatic women," *Australian & New Zealand Journal of Obstetrics & Gynaecology* 49(5), 448-450.

Nelson, H. D. et al. (2009) "Screening for Breast Cancer: An Update for the U.S. Preventive Services Task Force," *Annals of Internal Medicine* 151(10), 727-737.

Nguyen, D. H. et al. (2005) "Effects of Natural Human Antibodies against a Nonhuman Sialic Acid That Metabolically Incorporates into Activated and Malignant Immune Cells," *The Journal of Immunology* 175(1), 228-236.

Nogueira, L. et al. (2009) "Prostatic specific antigen for prostate cancer detection," *International Braz j urol* 35(5), 521-529.

Nossov, V. et al. (2008) "The early detection of ovarian cancer: from traditional methods to proteomics. Can we really do better than serum CA-125?," *American Journal of Obstetrics and Gynecology* 199(3), 215-223.

Ogata, S. et al. (1998) "Different modes of sialyl-Tn expression during malignant transformation of human colonic mucosa," *Glycoconjugate Journal* 15(1), 29-35.

Oppmann, B. et al. (2000) "Novel p19 Protein Engages IL-12p40 to Form a Cytokine, IL-23, with Biological Activities Similar as Well as Distinct from IL-12," *Immunity* 13(5), 715-725.

Ostrand-Rosenberg, S. (2008) "Immune surveillance: a balance between protumor and antitumor immunity," *Current Opinion in Genetics & Development* 18(1), 11-18.

Oyelaran, O. et al. (2009) "Profiling Human Serum Antibodies with a Carbohydrate Antigen Microarray," *Journal of Proteome Research* 8(9), 4301-4310.

Padler-Karavani, V. et al. (2008) "Diversity in specificity, abundance, and composition of anti-Neu5Gc antibodies in normal humans: Potential implications for disease," *Glycobiology* 18(10), 818-830.

Parkin, D. M. et al. (2001) "Cancer burden in the year 2000. The global picture," *European Journal of Cancer* 37, Supplement 8(0), 4-66.

Pitot, H. C. (1978) "The Language of Oncology," in *Fundamentals of Oncology* (Dekker, M., Ed.), pp. 15-28, New York.

Prehn, R. T. et al. (2008) "The flip side of immune surveillance: immune dependency," *Immunological Reviews* 222(1), 341-356.

Raedle, J. et al. (1998) "Clinical evaluation of autoantibodies to p53 protein in patients with chronic liver disease and hepatocellular carcinoma," *European Journal of Cancer* 34(8), 1198-1203.

Ransohoff, D. F. (2004) "Rules of evidence for cancer molecular-marker discovery and validation," *Nature Reviews Cancer* 4(4), 309-314.

Rudd, P. M. et al. (2008) "Glycosylation changes on serum glycoproteins in ovarian cancer may contribute to disease pathogenesis," *Disease Markers* 25(4/5), 219-232.

(56) References Cited

OTHER PUBLICATIONS

Schröder, F. H. et al. (2009) "Screening and Prostate-Cancer Mortality in a Randomized European Study," *New England Journal of Medicine* 360(13), 1320-1328.
Sewell, R. et al. (2006) "The ST6GalNAc-I Sialyltransferase Localizes throughout the Golgi and Is Responsible for the Synthesis of the Tumor-associated Sialyl-Tn O-Glycan in Human Breast Cancer," *Journal of Biological Chemistry* 281(6), 3586-3594.
Sing, T. et al. (2005) "ROCR: visualizing classifier performance in R," *Bioinformatics* 21(20), 3940-3941.
Singer, O. et al. (2005) "Targeting BACE1 with siRNAs ameliorates Alzheimer disease neuropathology in a transgenic model," *Nature Neuroscience* 8(10), 1343-1349.
Slovin, S. F. et al. (2005) "Carbohydrate vaccines as immunotherapy for cancer," *Immunology & Cell Biology* 83(4), 418-428.
Soussi, T. (2000) "p53 Antibodies in the Sera of Patients with Various Types of Cancer: A Review," *Cancer Research* 60(7), 1777-1788.
Srivastava, S. et al. (2002) "Biomarkers in Cancer Screening: A Public Health Perspective," *The Journal of Nutrition* 132(8), 2471S-2475S.
Stacker, S. A. et al. (1985) "A new breast carcinoma antigen defined by a monoclonal antibody," *Journal of the National Cancer Institute* 75(5), 801-811.
Tan, H. T. et al. (2009) "Serum autoantibodies as biomarkers for early cancer detection," *FEBS Journal* 276(23), 6880-6904.
Tangvoranuntakul, P. et al. (2003) "Human uptake and incorporation of an immunogenic nonhuman dietary sialic acid," *Proceedings of the National Academy of Sciences* 100(21), 12045-12050.
Taylor, R. E. et al. (2010) "Novel mechanism for the generation of human xeno-autoantibodies against the nonhuman sialic acid N-glycolylneuraminic acid," *The Journal of Experimental Medicine* 207(8), 1637-1646.
Thompson Im, A. D. C. C. et al. (2005) "Operating characteristics of prostate-specific antigen in men with an initial psa level of 3.0 ng/ml or lower," *JAMA: The Journal of the American Medical Association* 294(1), 66-70.
Tiscornia, G. et al. (2006) "Production and purification of lentiviral vectors," *Nature Protocols* 1(1), 241-245.
Uygur-Bayramicli, O. et al. (2007) "Type 2 diabetes mellitus and CA 19-9 levels," *World Journal of Gastroenterology* 13(40), 5357-5359.
Van Leeuwen, P. J. et al. (2010) "Prostate cancer mortality in screen and clinically detected prostate cancer: Estimating the screening benefit," *European Journal of Cancer* 46(2), 377-383.
Varki, A. (2001) "N-glycolylneuraminic acid deficiency in humans," *Biochimie* 83(7), 615-622.
Varki, A. (2009) "Multiple changes in sialic acid biology during human evolution," *Glycoconjugate Journal* 26(3), 231-245.
Varki, A. (2010) "Uniquely human evolution of sialic acid genetics and biology," *Proceedings of the National Academy of Sciences* 107(Supplement 2), 8939-8946.
Varki, A. et al. (2009) "Glycosylation Changes in Cancer," in *Essentials of Glycobiology* (Varki, A., et al., Eds.), pp. 617-632, Cold Spring Harbor Laboratory Press, Cold Spring Harbor, New York.

Weiss, J. M. et al. (2007) "Immunotherapy of Cancer by IL-12-based Cytokine Combinations," *Expert Opinion on Biological Therapy* 7(11), 1705-1721.
Wu, C.-Y. et al. (2009) "New development of glycan arrays," *Organic & Biomolecular Chemistry* 7(11), 2247-2254.
Wu, X. et al. (2004) "A New Homobifunctional p-Nitro Phenyl Ester Coupling Reagent for the Preparation of Neoglycoproteins," *Organic Letters* 6(24), 4407-4410.
Yonezawa, S. et al. (1992) "Sialosyl-Tn antigen. Its distribution in normal human tissues and expression in adenocarcinomas.," *American Journal of Clinical Pathology* 98(2), 167-174.
Yu, H. et al. (2005) "A Multifunctional Pasteurella multocida Sialyltransferase: A Powerful Tool for the Synthesis of Sialoside Libraries," *Journal of the American Chemical Society* 127(50), 17618-17619.
Yu, H. et al. (2006) "One-pot three-enzyme chemoenzymatic approach to the synthesis of sialosides containing natural and non-natural functionalities," *Nature Protocols* 1(5), 2485-2492.
Yu, H. et al. (2007) "Efficient chemoenzymatic synthesis of biotinylated human serum albumin-sialoglycoside conjugates containing O-acetylated sialic acids," *Organic & Biomolecular Chemistry* 5(15), 2458-2463.
Yu, H. et al. (2006) "Highly Efficient Chemoenzymatic Synthesis of Naturally Occurring and Non-Natural $\alpha$-2,6-Linked Sialosides: A P. damsela $\alpha$-2,6-Sialyltransferase with Extremely Flexible Donor—Substrate Specificity," *Angewandte Chemie International Edition* 45(24), 3938-3944.
Zhang, D. et al. (2009) "Proteomics, pathway array and signaling network-based medicine in cancer," *Cell Division* 4(1), 20.
Padler-Karavani, et al., "Human Xeno-Autoantibodies against a Non-Human Sialic Acid Serve as Novel Serum Biomarkers and Immunotherapeutics in Cancer", *Cancer Research*, 71(9):3352-3363 (2011).
Padler-Karavani, et al., "Human Xeno-Autoantibodies against a Non-Human Sialic Acid Serve as Novel Serum Biomarkers and Immunotherapeutics in Cancer", *Cancer Research*, 71(9):3352-3363, 1-19 Supplemental Data (2011).
Hedlund, et al. "Evidence for a human-specific mechanism for diet and antibody-mediated inflammation in carcinoma progression." PNAS, 105(48):1-2, Supporting Information (2008).
Koda, et al., "Application of Tyramide Signal Amplification for Detection of N-Glycolylneuraminic Acid in Human Hepatocellular Carcinoma." *Int J Clin Oncol*, 8(5):317-321 (2003).
Naito, et al., "Germinal center marker GL7 probes activation-dependent repression of n-glycoylneuraminic acid, a sialic acid species involved in the negative modulation of B-cell activation." *Mol. Cell. Biol.*, 27(8):3008-3022 (2007).
Liu, et al., "Integrative disease classification based on cross-platform microarray data." *BMC Bioinformatics*, 10 Suppl 1, S25 (2009).
Saldova, et al., Glycosylation changes on serum glycoproteins in ovarian cancer may contribute to disease pathogenesis. Dis Markers 25, 219-232 (2008).

* cited by examiner

COMPOSITIONS AND METHODS FOR DETECTING CANCER

This application is a divisional of co-pending U.S. application Ser. No. 13/007,237, filed on Jan. 14, 2011, which claims priority to U.S. provisional Application Ser. No. 61/295,386, filed Jan. 15, 2010, each of which is herein incorporated by reference in its entirety for all purposes.

This invention was made with government support under grant U01 CA128442-01, awarded by the National Institutes of Health (NIH) and HHSN261200700063C awarded by National Cancer Institute Small Business Invention Research (NCI SBIR). The government has certain rights in the invention.

FIELD OF INVENTION

The invention provides sialylated glycans and antibodies that specifically bind to them. The invention's compositions and methods for using them are useful for early detection and diagnosis of cancer.

BACKGROUND

Cancer is a leading cause of death worldwide, and mortality is largely attributed to cancers of epithelial origin, i.e., carcinomas of the lung, colon, breast, liver, stomach, prostate, ovary, endometrium and pancreas (Parkin et al., 2001). Survival rates are dramatically improved when carcinomas are diagnosed early and the disease is limited to the organ of origin. Indeed, physical methods for screening like pap smears in cervical cancer and mammography in breast cancer have dramatically reduced mortality rates (Marcial, 1977, Nelson et al., 2009b). Thus, research towards developing new early detection biomarkers in easily accessible body fluids, such as serum, urine or saliva has been encouraged (Srivastava and Gopal-Srivastava, 2002). Some well-known biomarkers (Nossov et al., 2008, Candefjord et al., 2009, Greene et al., 2009, Gupta and L is, 2009, Nelson et al., 2009a, Nogueira et al., 2009, van Leeuwen et al., 2009) are reliably detected in advanced stages of disease, but lack sufficient sensitivity and especially specificity for early cancer diagnosis, and are thus used mainly for prognosis, staging, monitoring and selection of therapy (Ludwig and Weinstein, 2005).

An alternative promising strategy is to take advantage of the immune response to cancer, which can be elicited at an early stage during tumorigenesis. This is partially manifested by production of autoantibodies against tumor-associated antigens (Raedle et al., 1998, Soussi, 2000, Desmetz et al., 2009a, Desmetz et al., 2009b, Tan et al., 2009). However, specificity and sensitivity have been limited mainly owing to the heterogenous nature of cancer, where different proteins are aberrantly processed or regulated in patients with the same type of cancer, causing much variability in the immune response (Raedle et al., 1998, Soussi, 2000, Tan et al., 2009).

Novel serum biomarkers for cancer screening are needed, since current ones lack sufficient sensitivity and especially specificity for early diagnosis (18, 19), being reliably detected mainly in advanced stages, and thus used more for prognosis, staging, monitoring and therapy selection (18). While antibodies against tumor-associated antigens are commonly found in cancer patients at an early stage and could potentially be sensitive detectors for malignant transformation (21, 22), none of the previously described autoantibodies show sufficient specificity in screening.

Available blood based assays have minimal clinical utility for the early diagnosis of cancer due to poor sensitivity and specificity. Generally they are used for monitoring the treatment of metastatic cancer. Prostate specific antigen (PSA), which is widely used to screen for prostate cancer, is the best example of a useful blood based cancer screening assay and in recently published randomized studies has marginal clinical utility. The following blood based cancer tests are used; PSA, CA27.29, CA19.9, CA125, CEA, and αFP. Aside from PSA only αFP is used as a screening test, in this case for patients with hepatitis C induced cirrhosis at high risk for hepatocellular carcinoma. None of these tests has been shown to reduce cancer specific mortality with a reasonable financial or morbidity cost. Nevertheless, PSA and αFP screening as well as CA125 screening are often used due to the profound need for blood based cancer screening.

Despite advances in the art, there remains a need for improved biomarkers for cancer screening.

SUMMARY OF THE INVENTION

The invention provides a method for detecting cancer in a subject, comprising determining, in a biological sample obtained from the subject, the level of one or more compounds selected from the group of a) Neu5Gc-sialylated antigen, b) epitope of the Neu5Gc-sialylated antigen, c) derivative of the Neu5Gc-sialylated antigen, and d) antibody that specifically binds to one or more of the antigen, the epitope, and the derivative, wherein the subject is identified as having cancer when a higher level of one or more of the compounds is detected relative to a control normal sample, and the subject is identified as being cancer-free when none of the levels of the compounds is higher than a control normal sample. In one embodiment, the Neu5Gc-sialylated antigen is selected from the group of i) Neu5Gc-sialylated glycan, ii) Neu5Gc-sialylated-Le$^x$, and iii) Neu5Gc-sialylated-Le$^a$. In a particular embodiment, the Neu5Gc-sialylated glycan is selected from the group of Neu5Gcα2-6GalNAcα-R (Glycan 6), Neu5Gc9Acα2-3Galβ1-4GlcNAcβ-R (Glycan 2), Neu5Gcα2-6Lacβ-R (Glycan 20), and Neu5Gcα2-3Galβ1-3GalNAcβ-R (Glycan 34), Neu5Gcα2-6GalNAcα-OR (Glycan 6), Neu5Gc9Acα2-3Galβ1-4GlcNAcβ-OR (Glycan 2), Neu5Gcα2-6Lacβ-OR (Glycan 20), and Neu5Gcα2-3Galβ1-3GalNAcβ-OR (Glycan 34), wherein R is selected from the group of biotin, albumin, ProNH2, —CH—, —OH, —OCH$_3$, —OCH$_2$—CH$_3$, —H, hydrido, hydroxy, alkoxyl, oxygen, carbon, sulfur, nitrogen, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxy-groups, hydrazide groups, amino lipid 1,2-dihexadecyl-sn-glycero-3-phosphoethanolamine (DHPE), aminooxy (AO) functionalized DHPE, glycosylphosphatidylinositol (GPI), and wherein Lac is Galβ1-4GlcNAc. In one preferred embodiment, the Neu5Gc-sialylated glycan comprises Neu5Gcα2-6GalNAcα-R (Glycan 6). In an alternative embodiment, the Neu5Gc-sialylated-Le$^x$ comprises Neu5Gcα2-3Galβ1-4(Fucα1-3)GlcNAc). In yet another embodiment, the Neu5Gc-sialylated-Le$^a$ comprises one or more of (Neu5Gcα2-3Galβ1-3(Fucα1-4)GlcNAc and 9-O-acetyl-G$_{D3}$ (Neu-5,9Ac$_2$α2-8Neu5Acα2-3Galβ1-4Glcβ1Ceramide). While not intending to limit the antibody to any particular type or specificity, in one embodiment, the antibody specifically binds to a Neu5Gc-sialylated glycan that comprises Neu5Gcα2-6GalNAcα-R (Glycan 6). In a further embodiment, the determining step comprises detecting antibody that specifically binds to one or more of the Neu5Gc-sialylated antigen, the epitope of the antigen, and the derivative of the antigen. In some embodiments, the subject is indicated for initiation of anti-cancer therapy when an increase in the level of one or more of the compounds is detected. In alternative embodiments, the subject is indicated for confirmatory diagnostic cancer testing an increase in the level of one or more of the compounds is detected. In yet further embodiments, the methods of the invention further comprise initiating anti-cancer therapy in a subject having an increase in the level of one or more of the compounds. In particular embodiments, the method may further comprise performing a confirmatory diagnostic cancer test in a subject having an increase in the level of one or more of the compounds. In some embodiments, the subject lacks detectable symptoms of cancer, has one or more detectable symptom of cancer, and/or is at risk of cancer. In particular embodiments, the cancer comprises a carcinoma. In alternative embodiments, the cancer is selected from the group of breast cancer, prostate cancer, ovary cancer, lung cancer, colon cancer, pancreatic cancer, endometrial cancer. In particular embodiments, the invention's methods further comprise treating the subject to reduce one or more symptoms of the cancer. In further embodiments, the antibody specifically binds to a Neu5Gc-sialylated glycan that comprises Neu5Gc$\alpha$2-6GalNAc$\alpha$-R (Glycan 6). In another embodiment, the antibody has an area under the curve (AUC) for a Receiver Operator Characteristic (ROC) curve of cancer of greater than 0.50 and/or has a cancer specificity greater than 50%, and/or has a cancer sensitivity greater than 50%.

The invention further provides an isolated Neu5Gc-sialylated antigen selected from the group of i) Neu5Gc-sialylated glycan, ii) Neu5Gc-sialylated-Le$^x$, and iii) Neu5Gc-sialylated-Le$^a$.

Additionally provided herein is an antibody that specifically binds to one or more Neu5Gc-sialylated antigens described herein.

The invention also provides an antibody that specifically binds to one or more antibody that specifically binds to one or more Neu5Gc-sialylated antigens described herein.

Also provided by the invention is a kit comprising a composition that contains one or more of the Neu5Gc-sialylated antigens described herein, and/or one or more antibody described herein. In some embodiments, one or more of the Neu5Gc-sialylated antigens is comprised in an array.

DEFINITIONS

Figure 1:
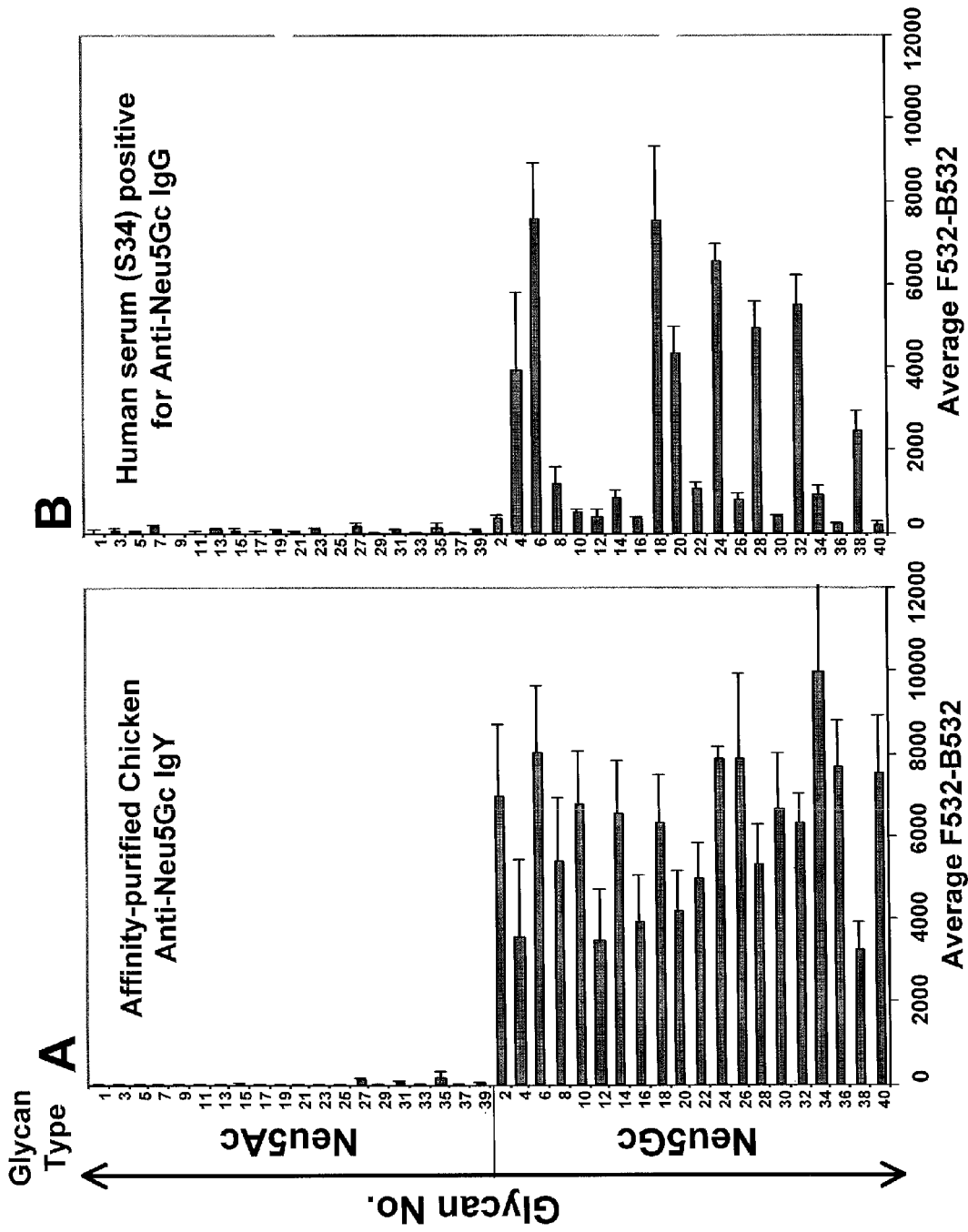
FIG. 1. Validation of sialoglycan-microarray slides for detection of anti-Neu5Gc antibodies. Various glycan-pairs (glycans #1-40 as detailed in Table 2) with terminal Neu5Gc or Neu5Ac were spotted on Epoxy-coated slides, then developed using (A) affinity-purified chicken anti-Neu5Gc IgY (1:10,000) (34) detected by Cy3-anti-chicken IgY (0.5 μg/ml); or, (B) human anti-Neu5Gc Ig positive human serum (1:100; S34 (5) detected by Cy3-anti-human IgG (1.5 μg/ml). Data were analyzed with an Excel pivot table, are representative of more than three independent experiments and show mean±SD of 4 replicate spots (of the glycans printed at 125 μM).

To facilitate understanding of the invention, a number of terms are defined below.

The terms "purified," "isolated," and grammatical equivalents thereof as used herein, refer to the reduction in the amount of at least one undesirable component (such as cell type, protein, and/or nucleic acid sequence) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in "enrichment," i.e., an increase in the amount of a desirable cell type, protein and/or nucleic acid sequence in the sample. In one embodiment, the present invention contemplates purified or isolated sialylated glycans.

As used herein, the terms "treat", "treating", "treatment" and grammatical equivalents refers to combating a disease or disorder, as for example in the management and care of a patient. In one embodiment, treating a disease (e.g., cancer, metastasis, etc.) includes reducing one or more symptoms of the disease.

As used herein, the terms "diagnose", "diagnosis" or "diagnosing" refers to the recognition of a disease by its signs and symptoms (e.g., resistance to conventional therapies), or genetic analysis, pathological analysis, histological analysis, and the like.

As used herein, the terms "cancer cell" and "tumor cell" refer to a cell undergoing early, intermediate or advanced stages of multi-step neoplastic progression as previously described (Pitot et al., Fundamentals of Oncology, 15-28 (1978)), herein incorporated by reference. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as a "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell". A dysplastic cell resembles an immature epithelial cell, is generally spatially disorganized within the tissue and loses its specialized structures and functions. During the intermediate stages of neoplastic progressions an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive i.e., they either invade adjacent tissues, or are shed from the primary site and circulate through the blood and lymph to other locations in the body where they initiate secondary cancers. Cancer includes, for example, carcinomas such as lung cancer, breast cancer, prostate cancer, cervical cancer, pancreatic cancer, colon cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia. Malignant neoplasms are further exemplified by sarcomas (such as osteosarcoma and Kaposi's sarcoma).

The term "cancer" or "neoplasia" refers to a plurality of cancer cells.

A "cancer at risk for metastases" refers to a cancer that may differentiate into a metastatic cancer. Such risk may be based on family history, genetic factors, type of cancer, environmental factors, etc.

"Carcinoma" refers to a malignant new growth made up of epithelial cells tending to infiltrate the surrounding tissues and give rise to metastases.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

A "subject" and "animal" that may benefit from the invention's methods interchangeably includes any multicellular animal, preferably a mammal. Mammalian subjects include humans, non-human primates, murines, ovines, bovines, ruminants, lagomorphs, porcines, caprines, equines, canines, felines, ayes, etc.). Thus, non-human mammalian subjects are exemplified by mouse, rat, guinea pig, hamster, ferret and chinchilla.

"Subject in need of" reducing one or more symptoms of a disease, e.g., in need of reducing cancer metastasis and/or in need of reducing one or more symptoms of cancer, includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable).

Subject "at risk" for disease (such as cancer) refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

The terms "sample" and "specimen" as used herein are used in their broadest sense to include any composition that is obtained and/or derived from biological or environmental source, as well as sampling devices (e.g., swabs) that are brought into contact with biological or environmental samples. "Biological samples" include those obtained from an animal, including body fluid samples such as serum, plasma, blood, urine, cerebrospinal fluid (CSF), sputum, saliva, cell extract, tissue extract, etc., as well as solid samples such as tissue (such as biopsy material), cells, and the like.

The term "antibody" encompasses any immunoglobulin (e.g., IgG, IgM, IgA, IgE, IgD, etc.) obtained from any source (e.g., birds, humans, rodents, non-human primates, caprines, bovines, equines, ovines, etc.). Included within this definition are polyclonal antibody, monoclonal antibody, and chimeric antibody. "Polyclonal antibody" refers to an immunoglobulin produced from more than a single clone of plasma cells; in contrast "monoclonal antibody" refers to an immunoglobulin produced from a single clone of plasma cells. A "chimeric antibody" contains portions of two different antibodies, typically of two different species. See, e.g.: U.S. Pat. No. 4,816, 567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al.

The terms "antigen," "immunogen," "antigenic," "immunogenic," "antigenically active," "immunologic," and "immunologically active" when made in reference to a molecule, refer to any substance that is capable of inducing a specific humoral immune response (including eliciting a soluble antibody response) and/or cell-mediated immune response (including eliciting a CTL response).

In one embodiment, the antigen comprises an epitope. The terms "epitope" and "antigenic determinant" refer to a structure on an antigen, which interacts with the binding site of an antibody or T cell receptor as a result of molecular complementarity. An epitope may compete with the intact antigen, from which it is derived, for binding to an antibody. Generally, secreted antibodies and their corresponding membrane-bound forms are capable of recognizing a wide variety of substances as antigens, whereas T cell receptors are capable of recognizing only fragments of proteins which are complexed with MHC molecules on cell surfaces. Antigens recognized by immunoglobulin receptors on B cells are subdivided into three categories: T-cell dependent antigens, type 1 T cell-independent antigens; and type 2 T cell-independent antigens. Also, for example, when a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody The terms "specific binding," "binding specificity," and grammatical equivalents thereof when made in reference to the binding of a first molecule (such as a polypeptide, glycoprotein, nucleic acid sequence, polysaccharide, antigen, etc.) to a second molecule (such as a polypeptide, glycoprotein, nucleic acid sequence, polysaccharide, antibody etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule. For example, if a second molecule is specific for structure "A" that is on or within a first molecule, the presence of a third nucleic acid sequence containing structure A will reduce the amount of the second molecule which is bound to the first molecule.

"Specificity" of a method and/or molecule for disease, such as "specificity for cancer" which is interchangeably used with "cancer specificity", refers to the proportion (e.g., percentage, fraction, etc.) of negatives (i.e., healthy individuals not having disease) that are correctly identified, i.e., the percentage of healthy subjects who are correctly identified as not having disease. Specificity may be calculated according to the following equation:

Specificity=number of true negatives/(number of true negatives+number of false positives).

Thus, in some embodiments, the invention's compositions and/or methods have a "cancer specificity" greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% specificity is most desirable, i.e., not predicting anyone from the healthy group as having cancer, it is not necessary. Data herein show that in some embodiments, the false positive rate (sensitivity) and the false negative rate (specificity) were both ⅕=20% (Example 4). In another embodiment, data herein show that the sensitivity was 37/176=21.1% and the specificity was 34/60=68% (Example 5). In a further embodiment, when the sensitivity was 0.25, the mean specificity was 0.79 (Example 7). In yet another embodiment, when the sensitivity was 0.2 and 0.3, the mean specificity is 0.84 and 0.75, respectively (Example 8). Additional specificity values are shown in Example 9.

Figure 2:
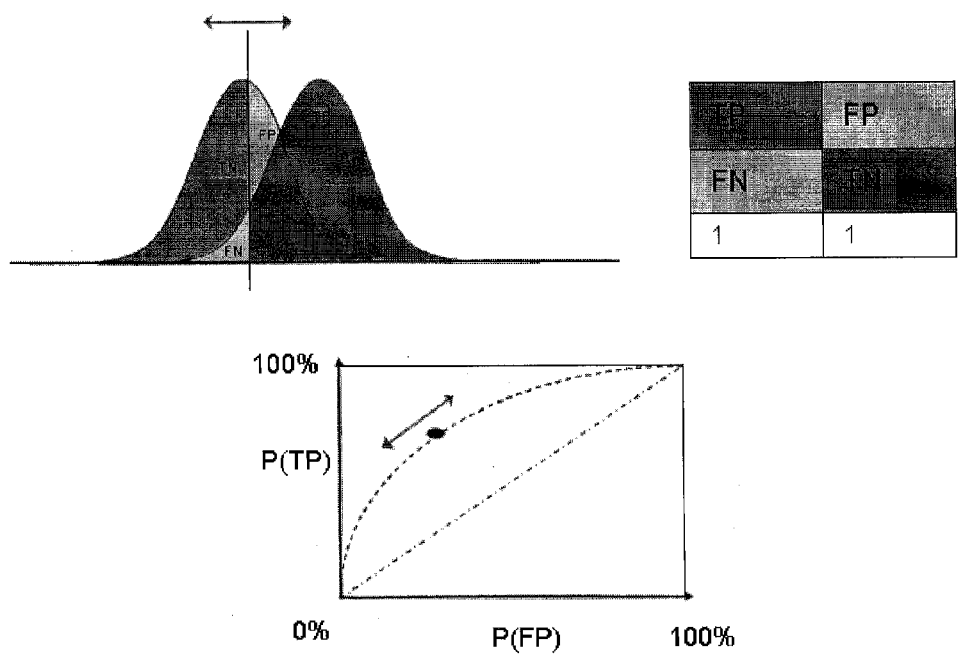
FIG. 2. Receiver Operating Characteristic ("ROC") curve. In the upper left panel is a simplified graphical representation of a binary classification test. TP is true positive, FP is false positive, FN is false negative, and TN is true negative.

In alternative embodiments, specificity is expressed (together with sensitivity) as a statistical measure of the performance of a binary classification test, such as using a Receiver Operator Characteristic (ROC) curve". For any test, there is usually a trade-off between specificity and sensitivity. For example: in cancer screening tests of human subjects, it is undesirable to risk falsely identifying healthy people as having cancer (low specificity), due to the high costs. These costs are both physical (unnecessary risky procedures) and financial. This trade-off can be represented graphically using a ROC curve (FIG. 2). "Receiver Operator Characteristic curve" and "ROC curve" refer to a plot of the true positive rate (AKA sensitivity) versus true negative rate (AKA 1-specificity). The measured result of the test is represented on the x axis while the y axis represents the number of control (e.g., healthy) or case (e.g., cancer) subjects. For any given cut point (each point along the x axis) a sensitivity and specificity of the assay can be measured. The range of sensitivity and specificity for any given assay can range from 0% to 100%, depending on the selected cut point. For this reason, in some preferred embodiments, the AUC is used as the standard measure of an assay's specificity and/or sensitivity. The "area under the curve" ("AUC") for the ROC curve plot is equal to the probability that a classifier will rank a randomly chosen positive instance higher than a randomly chosen negative one. Thus, AUC is a general measure of a tests ability to successfully discriminate between case (e.g., cancer) and control (e.g., healthy) subjects. Random chance would generate an AUC of 0.5. Therefore, in one embodiment, useful tests preferably have AUC's greater than 0.50, including any value from 0.51 to 1.00, such as from 0.55 to 1.00, from 0.60 to 1.00, from 0.65 to 1.00, from 0.70 to 1.00, from 0.75 to 1.00, from 0.80 to 1.00, from 0.85 to 1.00, from 0.90 to 1.00, from 0.95 to 1.00, and most preferably 1.00. AUC values greater than 0.50 include 0.51, 0.52, 0.52, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, and 0.99. Data herein show that anti-GcSTn antibodies gave an AUC of 0.67 and 0.60 on two independent sets of breast cancer subjects versus female controls and an AUC of 0.69 on an independent set of lung, ovary, pancreatic, endometrial, prostate and colon cancers versus controls. Internal cross validation confirms these results with mean AUCs of 0.63, 0.68 and 0.67 respectively. Based on a very stringent permutation test of the internal cross validation the 96% confidence intervals for the mean AUC of each independent set was determined. These were 0.29-0.91, 0.167-0.917, and 0.283-0.817 for the training breast cancer set, the validation breast cancer set and for the other cancer validation set respectively.

"Sensitivity" of a method and/or molecule for disease, such as "sensitivity for cancer" which is interchangeably used with "cancer sensitivity," refers to the proportion (e.g., percentage, fraction, etc.) of positives (i.e., individuals having cancer) that are correctly identified as such (e.g. the percentage of people with cancer who are identified as having the condition). Sensitivity may be calculated according to the following equation;

Sensitivity=number of true positives/(number of true positives+number of false negatives).

Thus, in some embodiments, the invention's compositions and/or methods have a "cancer sensitivity" greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% sensitivity is most desirable (i.e., predicting all subjects from the cancer group as having cancer), it is not necessary.

In alternative embodiments, the invention's compositions and/or methods have a "cancer sensitivity" equal to or lower than 50%, including any numerical value from 0% to 50%, such as 1%, 2%, 3%, 4%, 6%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, and 49%. Data herein show that in some embodiments, the false positive rate (sensitivity) and the false negative rate (specificity) were both ⅙=20% (Example 4). In another embodiment, data herein show that the sensitivity was 37/176=21.1% and the specificity was 34/60=68% (Example 5). In a further embodiment, when the sensitivity was 0.25, the mean specificity was 0.79 (Example 7). In yet another embodiment, when the sensitivity was 0.2 and 0.3, the mean specificity is 0.84 and 0.75, respectively (Example 8). Additional sensitivity values are shown in Example 9.

In some embodiments, sensitivity is expressed (together with specificity) as a statistical measure of the performance of a binary classification test, such as using AUC of a ROC curve, as discussed above with respect to specificity.

"Glycan" refers to a polysaccharide or oligosaccharide. Glycan may also be used to refer to the carbohydrate portion of a glycoconjugate, such as a glycoprotein, glycolipid, or a proteoglycan. Glycans usually consist of O-glycosidic linkages of monosaccharides. For example, cellulose is a glycan (or more specifically a glucan) composed of beta-1,4-linked D-glucose, and chitin is a glycan composed of beta-1,4-linked N-acetyl-D-glucosamine. Glycans can be homo or heteropolymers of monosaccharide residues, and can be linear or branched. Glycans tested in the instant invention are shown in Table 3.

"Sialylated" and "sialyl" compound (e.g., sialylated antigen, sialylated glycan, sialylated Le$^x$, and sialylated Le$^a$) interchangeably refer to a compound containing sialic acid.

"Neu5Gc-sialylated" compound (e.g., Neu5Gc-sialylated antigen, Neu5Gc-sialylated glycan, Neu5Gc-sialylated Le$^x$, and Neu5Gc-sialylated Le$^a$) refers to a sialylated compound containing a terminal N-glycolylneuraminic acid ("Neu5Gc"). In contrast, "Neu5Ac-sialylated" compound (e.g., Neu5Ac-sialylated antigen, Neu5Ac-sialylated glycan, Neu5Ac-sialylated Le$^x$, and Neu5Ac-sialylated Le$^a$) refers to a sialylated compound containing N-Acetylneuraminic acid (Neu5Ac). For example, "Neu5Gc-sialylated glycans" are exemplified by Neu5Gcα2-6GalNAcα-R (Glycan 6), wherein "R" is exemplified by the group of biotin, albumin, ProNH$_2$, —CH—, —OH, —OCH$_3$, —OCH$_2$—CH$_3$, —H, hydrido, hydroxy, alkoxyl, oxygen, carbon, sulfur, nitrogen, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxy-groups, hydrazide groups, amino lipid 1,2-dihexadecyl-sn-glycero-3-phosphoethanolamine (DHPE), aminooxy (AO) functionalized DHPE, glycosylphosphatidylinositol (GPI). Without intending to limit the source or nature of "R", this includes structures that affect the physical spacing of the GcSTn. In some embodiments, the R group in combination with underlying substrates effect GcSTn spacing "Neu5Gc-sialylated antigen" includes Neu5Gc-sialylated glycan, Neu5Gc-sialylated Le$^x$, and Neu5Gc-sialylated Le$^a$, and refers to immunogenic extended glycan chains containing a terminal N-glycolylneuraminic acid ("Neu5Gc").

"Neu5Gc-sialylated glycan" is exemplified by GcSTn, Neu5Gcα2-6GalNAcα-R (Glycan 6), Neu5Gc9Acα2-3Galβ1-4GlcNAcβ-R (Glycan 2), Neu5Gcα2-6Lacβ-R (Glycan 20), and Neu5Gcα2-3Galβ1-3GalNAcβ-R (Glycan 34), Neu5Gcα2-6GalNAcα-OR (Glycan 6), Neu5Gc9Acα2-3Galβ1-4GlcNAcβ-OR (Glycan 2), Neu5Gcα2-6Lacβ-OR (Glycan 20), and Neu5Gcα2-3Galβ1-3GalNAcβ-OR (Glycan 34), wherein R is selected from the group consisting of biotin, albumin, ProNH2, —CH—, —OH, —OCH$_3$, —OCH$_2$—CH$_3$, —H, hydrido, hydroxy, alkoxyl, oxygen, carbon, sulfur, nitrogen, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxy-groups, hydrazide groups, amino lipid 1,2-dihexadecyl-sn-glycero-3-phosphoethanolamine (DHPE), aminooxy (AO) functionalized DHPE, glycosylphosphatidylinositol (GPI), and wherein Lac is Galβ1-4GlcNAc. Without intending to limit the source or nature of "R", this includes structures that affect the physical spacing of the GcSTn. In some embodiments, the R group in combination with underlying substrates effect GcSTn spacing.

"Neu5Gc Sialylated probes" refers to extended glycan chains with a terminal N-glycolylneuraminic acid and a non-reducing end linker group that can be used to conjugate the probes to a substrate. Probes may be in solution or immobilized on a solid substrate, such as an array.

"Derivative" of a compound refers to a compound that has been altered by modification of one or more of its elements. For example, "derivative of sialylated glycan" refers to a sialylated glycan that has been altered by modification of one or more of its elements, including modifications in cancer, as exemplified by 9OAc-GcSTn.

The following terms are used interchangeably: "GcSTn," "Neu5Gc-Sialyl-Tn," "Neu5Gcα2-6GalNAcα1-O-Ser/Thr" and "disaccharide N-glycolylneuraminic acid-alpha2-6-N-acetylgalactosamine-alpha." GcSTn is one example of a Neu5Gc-sialylated antigen.

"Anti-Neu5Gc-Sialyl-Tn antibody" refers to an antibody that specifically binds to the invention's novel Neu5Gcα2-6GalNAcα1-O-Ser/Thr.

"N-glycolylneuraminic acid" and "Neu5Gc" are interchangeable.

"N-Acetylneuraminic acid" and "Neu5Ac" are interchangeably used, and refer to the hydroxylated form N-Glycolylneuraminic acid (Neu5Gc).

"Sialyl-Tn" and "STn" are interchangeably used to refer to a mucin carbohydrate-associated antigen (Neu5Acα2-6GalNAcα1-O-Ser/Thr) (SialicAcidα2-6GalNAcα1-O-Ser/Thr).

"Sialyl-Le$^x$" refers to Neu5Acα2-3Galβ1-4(Fucα-3)GlcNAc.

"Sialyl-Le$^a$" refers to the regioisomer of Sialyl-Lex (Neu5Acα2-3Galβ1-3(Fucα1-4)GlcNAc).

"9-O-acetyl-G$_D$3" refers to Neu-5,9Ac$_2$α2-8Neu5Acα2-3Galβ1-4Glcβ1-1Ceramide.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, glycan, Neu5Gc-sialylated antigen (e.g., sialylated glycan), epitope of a Neu5Gc-sialylated antigen, derivative of a Neu5Gc-sialylated antigen, antibody (e.g., that specifically binds to one or more of a Neu5Gc-sialylated antigen, epitope of a eu5Gc-sialylated antigen, derivative of a Neu5Gc-sialylated antigen), etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence, glycan, Neu5Gc-sialylated antigen (e.g., sialylated glycan), epitope of a Neu5Gc-sialylated antigen, derivative of a Neu5Gc-sialylated antigen, antibody (e.g., that specifically binds to one or more of a Neu5Gc-sialylated antigen, epitope of a eu5Gc-sialylated antigen, derivative of a Neu5Gc-sialylated antigen), etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

The term "control" as used herein when in reference to a sample, cell, tissue, animal, etc., refers to any type of sample, cell, tissue, animal, etc. that one of ordinary skill in the art may use for comparing the results to another sample, cell, tissue, animal, etc., by maintaining the same conditions except in some one particular factor, and thus inferring the causal significance of this varied factor.

BRIEF DESCRIPTION OF THE INVENTION

The invention provides the discovery that when Neu5Gc replaces Neu5Ac in any sialylated antigen that is over-expressed in a human cancer, this generates a novel cancer-specific antigen and cancer-specific antibody response. Thus, the invention provides the discovery that cancer is correlated with replacement of naturally occurring Neu5Ac in any sialylated antigen, that is over-expressed in a human cancer, by Neu5Gc.

Thus, the invention provides cancer markers exemplified by a) Neu5Gc-sialylated antigens, b) epitopes of the Neu5Gc-sialylated antigens, c) derivatives of the Neu5Gc-sialylated antigen, and d) antibodies that specifically bind to one or more of the antigen, the epitope, and the derivative. The invention further provides methods for detecting cancer by detecting one or more of these cancer markers, such as by detecting antibody that specifically binds to one or more of the antigen, the epitope, and the derivative, and to the antibodies against these markers.

Human carcinomas can metabolically incorporate and present the dietary non-human sialic acid Neu5Gc, which differs from the human sialic acid N-acetylneuraminic acid (Neu5Ac) by one oxygen atom. Tumor-associated Neu5Gc can interacts with low levels of circulating anti-Neu5Gc antibodies, thereby facilitating tumor progression via chronic inflammation in a human-like Neu5Gc-deficient mouse model.

This polyclonal spectrum of human anti-Neu5Gc antibodies also includes potential cancer biomarkers. We characterized them in cancer and non-cancer patients' sera, using a novel sialoglycan-microarray presenting multiple Neu5Gc-glycans and control Neu5Ac-glycans. In an embodiment, antibodies against Neu5Gcα2-6GalNAcα1-O-Ser/Thr (Gc-STn) were found to be more prominent in patients with carcinomas than with other diseases. This unusual epitope arises from dietary Neu5Gc incorporation into the carcinoma marker Sialyl-Tn, and is the first example of such a novel mechanism for biomarker generation.

In one embodiment, the invention provides compositions and methods for detecting cancer in a subject, comprising detecting in a sample from the subject an increased level, relative to a control sample, of one or more Neu5Gc-sialylated antigen, epitope of the Neu5Gc-sialylated antigen, and derivative of the Neu5Gc-sialylated antigen, wherein the Neu5Gc-sialylated antigenis selected from the group of Neu5Gcα2-6GalNAcα-R (Glycan 6), Neu5Gc9Acα2-3Galβ1-4GlcNAcβ-R (Glycan 2), Neu5Gcα2-6Lacβ-R (Glycan 20), and Neu5Gcα2-3Galβ1-3GalNAcβ-R (Glycan 34), wherein R is any natural or unnatural molecule to which a glycan can be coupled, such as biotin, albumin, ProNH$_2$ (Table 3), —CH—, —OH, —OCH$_3$, —OCH$_2$—CH$_3$, hydrido, hydroxy, alkoxyl, oxygen, carbon, sulfur, nitrogen, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylami-nooxy-groups, hydrazide groups, amino lipid 1,2-dihexadecyl-sn-glycero-3-phosphoethanolamine (DHPE), aminooxy (AO) functionalized DHPE, glycosylphosphatidylinositol (GPI), etc., and wherein Lac is Galβ1-4GlcNAc, thereby detecting the presence of cancer in the subject. In some embodiments, the sialylated glycan is purified. In one embodiment, the method further comprises treating the subject. Data herein show that while anti-Neu5Gc antibodies with various specificities are prevalent in human sera, anti-Neu5Gc-Sialyl-Tn antibodies are consistently elevated in carcinoma patients compared to healthy controls (Table 3). In some embodiments, R is ProNH2, and the sialylated glycan is selected from the group of Neu5Gcα2-6GalNAcα-R (Glycan 6), Neu5Gc9Acα2-3Galβ1-4GlcNAcβ-R (Glycan 2), Neu5Gcα2-6Lacβ-R (Glycan 20), and Neu5Gcα2-3Galβ1-3GalNAcβ-R (Glycan 34). In a particularly preferred embodiment, the sialylated glycan comprises Neu5Gcα2-6GalNAcα-R (Glycan 6) and/or Neu5Gcα2-6GalNAcα-OR (Table 3).

In some embodiments, detecting sialylated glycan in a sample involves detecting the presence and/or level of an antibody that specifically binds to the sialylated glycan and/or specifically binds to an epitope thereof. The invention is not limited to a particular type, or method for determining the level, of antibody that specifically binds to the sialylated glycan. Indeed, generic methods for detecting N-glycolyl-neuraminic acid (Neu5Gc) and anti-Neu5Gc specific antibodies are known in the art (e.g., Varki et al. U.S. Patent Application 2007/0275409, published Nov. 29, 2007) and disclosed herein.

In particular embodiments, antibody that specifically binds to the sialylated glycan, binds at a lower level to one or more molecule selected from the group of N-glycolylneuraminic acid (Neu5Gc) and Sialyl-Tn (STn). In a more preferred embodiment, that antibody that specifically binds to the sialylated glycan does not specifically bind to one or more molecule selected from the group of N-glycolylneuraminic acid (Neu5Gc) and Sialyl-Tn (STn).

While the compositions and methods of the invention are not limited to any particular specificity and/or sensitivity, in one embodiment, the antibody that specifically binds to the sialylated glycan has an area under the curve (AUC) for a Receiver Operator Characteristic (ROC) curve of cancer of greater than 0.50. In another embodiment, the antibody that specifically binds to the sialylated glycan has a cancer specificity greater than 50% and/or cancer sensitivity greater than 50%. In other embodiments, the cancer sensitivity is equal to or lower than 50%.

One advantage of the invention's compositions and methods is early detection of cancer. Thus in one embodiment, the invention's compositions and methods may be applied to a subject that lacks detectable symptoms of cancer (useful in, for example, early screening), a subject at risk of cancer (useful in, for example, early screening), and a subject that has one or more detectable symptom of cancer (useful in, for example, confirmation of a diagnosis of cancer). Thus, in some embodiments, the invention's compositions and methods may be used to monitor the progress of cancer and/or cancer treatment.

The invention's compositions and methods may be used in connection with any cancer, such as carcinoma. Without intending to limit the cancer to any particular source, in some embodiments, the cancer is selected from prostate cancer, ovary cancer, lung cancer, colon cancer, pancreas cancer, and endometrium cancer. In another embodiment, the cancer is selected from the group of metastatic cancer (e.g., metastatic carcinoma) and non-metastatic cancer (e.g., non-metastatic carcinoma).

In some embodiments, the invention's methods employ the use of a control sample. Without limiting the type or source of control sample, in one embodiment, the control sample is from a tissue lacking cancer. This is exemplified by a control sample from the same or different subject, such as a subject matched for gender and/or age, subject having a benign tumor, etc.

The invention also provides isolated sialylated glycans selected from Neu5Gcα2-6GalNAcα-R (Glycan 23), Neu5Gc9Acα2-3Galβ1-4GlcNAcβ-R (Glycan 21), Neu5Gcα2-6Lacβ-R (Glycan 30), Neu5Gcα2-3Galβ1-3GalNAcβ-R (Glycan 37), Neu5Gcα2-6GalNAcα-OR (Glycan 23), Neu5Gc9Acα2-3Galβ1-4GlcNAcβ-OR (Glycan 21), Neu5Gcα2-6Lacβ-OR (Glycan 30), and Neu5Gcα2-3Galβ1-3GalNAcβ-OR (Glycan 37), wherein R is any natural or unnatural molecule to which a glycan can be coupled, such as biotin, albumin, ProNH2 (Table 3), —CH—, —OH, —OCH$_3$, —OCH$_2$—CH$_3$, —H, hydrido, hydroxy, alkoxyl, oxygen, carbon, sulfur, nitrogen, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxy-groups, hydrazide groups, amino lipid 1,2-dihexadecyl-sn-glycero-3-phosphoethanolamine (DHPE), aminooxy (AO) functionalized DHPE, glycosylphosphatidylinositol (GPI), etc., and wherein Lac is Galβ1-4GlcNAc. In one embodiment, the sialylated glycan is selected from Neu5Gcα2-6GalNAcα-ProNH$_2$ (Glycan 23), Neu5Gcα2-6LacβProNH$_2$ (Glycan 30), Neu5Gc9Acα2-3Galβ1-4GlcNAcβProNH2 (Glycan 21), and Neu5Gcα2-3Galβ1-3GalNAcβProNH2 (Glycan 37). The invention's sialylated glycans are useful as antigens for generating antibodies that specifically bind to the sialylated glycan. The anti-sialylated glycan antibodies in turn may be used to generate a secondary antibody that specifically binds to the anti-sialylated glycan antibody. These secondary antibodies are useful in detecting anti-sialylated glycan antibodies, such as those in samples from subjects being screened for cancer.

Also provided by the invention are anti-sialylated glycan antibodies that specifically bind to a sialylated glycan, epitope of the sialylated glycan, and derivative of the sialylated glycan, wherein the sialylated glycan is selected from Neu5Gcα2-6GalNAcα-R (Glycan 23), Neu5Gc9Acα2-3Galβ1-4GlcNAcβ-R (Glycan 21), Neu5Gcα2-6Lacβ-R (Glycan 30), Neu5Gcα2-3Galβ1-3GalNAcβ-R (Glycan 37), Neu5Gcα2-6GalNAcα-OR (Glycan 23), Neu5Gc9Acα2-3Galβ1-4GlcNAcβ-OR (Glycan 21), Neu5Gcα2-6Lacβ-OR (Glycan 30), and Neu5Gcα2-3Galβ1-3GalNAcβ-OR (Glycan 37), wherein R is any natural or unnatural molecule to which a glycan can be coupled, such as biotin, albumin, ProNH2 (Table 3), —OH, —OCH$_2$—CH$_3$, —H, hydrido, hydroxy, alkoxyl, oxygen, carbon, sulfur, nitrogen, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxy-groups, hydrazide groups, amino lipid 1,2-dihexadecyl-sn-glycero-3-phosphoethanolamine (DHPE), aminooxy (AO) functionalized DHPE, glycosylphosphatidylinositol (GPI), and wherein Lac is Galβ1-4GlcNAc. In a particular embodiment, the sialylated glycan is selected from Neu5Gcα2-6GalNAcαProNH2 (Glycan 23), Neu5Gcα2-6LacβProNH2 (Glycan 30), Neu5Gc9Acα2-3Galβ1-4GlcNAcβProNH2 (Glycan 21), and Neu5Gcα2-3Galβ1-3GalNAcβProNH2 (Glycan 37). As discussed above, the anti-sialylated glycan antibodies may be used to generate a secondary antibody that specifically binds to the anti-sialylated glycan antibody. These secondary antibodies are useful in detecting anti-sialylated glycan antibodies, such as those in samples from subjects being screened for cancer.

The invention further provides compositions and kits that contain one or more molecule selected from (a) one or more sialylated glycan, epitope of the sialylated glycan, and derivative of the sialylated glycan, wherein the sialylated glycan is selected from the group of Neu5Gcα2-6GalNAcα-R (Glycan 23), Neu5Gc9Acα2-3Galβ1-4GlcNAcβ-R (Glycan 21), Neu5Gcα2-6Lacβ-R (Glycan 30), and Neu5Gcα2-3Galβ1-3GalNAcβ-R (Glycan 37), Neu5Gcα2-6GalNAcα-OR (Glycan 23), Neu5Gc9Acα2-3Galβ1-4GlcNAcβ-OR (Glycan 21), Neu5Gcα2-6Lacβ-OR (Glycan 30), and Neu5Gcα2-3Galβ1-3GalNAcβ-OR (Glycan 37), wherein R is any natural or unnatural molecule to which a glycan can be coupled, such as biotin, albumin, ProNH2 (Table 3), —CH—, —OH, —OCH$_3$, —OCH$_2$—CH$_3$, —H, hydrido, hydroxy, alkoxyl, oxygen, carbon, sulfur, nitrogen, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxy-groups, hydrazide groups, amino lipid 1,2-dihexadecyl-sn-glycero-3-phosphoethanolamine (DHPE), aminooxy (AO) functionalized DHPE, glycosylphosphatidylinositol (GPI), etc., and wherein Lac is Galβ1-4GlcNAc, (b) an anti-sialylated glycan specific antibody, and (c) an antibody that specifically binds to the anti-sialylated glycan antibody.

DETAILED DESCRIPTION OF THE INVENTION

In one embodiment, the invention provides compositions and methods for cancer detection based on the discovery that xeno-autoantibodies against an immunogenic non-human dietary xeno-autoantigen can serve as a biomarker. Embodiments of the invention provides for the early detection of cancer, e.g. prior to detection of cancer by other methods such as mammography. Embodiments of the invention also provide for monitoring of cancer progression and treatment Embodiments of the invention are based upon the discovery that dietary Neu5Gc can metabolically replace Neu5Ac in STn, generating the unique neo-tumor-associated xeno-autoantigen GcSTn, specifically recognized by xeno-autoantibodies. This novel cancer biomarker is related to a metabolically-incorporated immunogenic dietary molecule. Embodiments of the invention further based on the observation that Neu5Gc can also replace Neu5Ac in other tumor-associated glycan structures, thereby generating other novel biomarkers, e.g. Gc-sialyl-Le$^x$, Gc-sialyl-Le$^a$ and Gc-9-O-acetyl-GD3. Examples of novel Neu5Gc-sialylated antigens are provided in Table 3 in Example 2 (see below).

In one embodiment, the invention provides the discovery that anti-GcSTn IgG is a unique human carcinoma-associated biomarker. Interestingly, glycan 6 resembles the carcinoma-associated biomarker Sialyl-Tn (STn; Neu5Acα2-6GalNAcα1-O-Ser/Thr), except that Neu5Ac is replaced with Neu5Gc (GcSTn; Neu5Gcα2-6GalNAcα1-O-Ser/Thr).

Data herein demonstrate that dietary Neu5Gc consumption by cancer patients replaces the terminal Neu5Ac of STn by Neu5Gc, generating the novel xeno-autoantigen GcSTn, along with its corresponding specific anti-GcSTn antibodies (FIG. 3D), as novel carcinoma biomarker (based on approximately 400 carcinoma patients and controls). These steps likely occur at an early tumor stage suggesting that anti-GcSTn antibodies are useful for early detection, or determining future risk, of carcinomas.

The invention provides compositions and methods for the detection of anti-GcSTn IgG as a useful biomarker for detection and monitoring of cancer, including but not limited to early detection of carcinomas. For example, an embodiment of the invention show detection of breast cancer with an estimated AUC of 0.6.

The invention provides compositions and methods that embody the discovery that Neu5Gc consumption by cancer patients metabolically replaces Neu5Ac by Neu5Gc, generating glycan xeno-autoantigens. The invention also provides compositions and methods that embody the discovery that the corresponding xeno-autoantibodies are unique tumor biomarkers.

In an embodiment, using a novel high-throughput sialoglycan-microarray containing multiple Neu5Gc-glycans with control Neu5Ac-matched glycans, we show that human serum antibodies against Neu5Gc-sialyl-Tn (GcSTn; Neu5Gcα2-6GalNAcα1-O-Ser/Thr) are enriched in carcinoma patients over controls.

Methods for detecting cancer specific antigens are known in the art (e.g., detection of prostate specific antigen (PSA) described in Robbins et al., U.S. Pat. No. 5,902,725, incorporated by reference in its entirety). However, unlike prostate specific antigen (PSA) the current invention is based, in some embodiments, on cancer specificity by Neu5Gc uptake, and/or Cosmc inactivation-dependent Neu5Gc incorporation into the invention's Neu5Gc-sialylated antigen (e.g., Gc-STn), and/or the human antibody response against the invention's Neu5Gc-sialylated antigen. In other words, by assaying xenoautoantibodies against the invention's Neu5Gc-sialylated antigen (e.g., Gc-STn) we can harness the amplification effect of the human immune response, increasing sensitivity for detection of the invention's occult Neu5Gc-sialylated antigen (e.g., Gc-STn). Additionally therapeutic maneuvers to reduce cancer risk by altering these antibody levels can be monitored and used to adjust treatment. Thus, the inventive compositions and methods may be used in the prediction of increased risk of developing cancer, early diagnosis of cancer, and pharmacodynamic monitoring of immune and/or dietary modulatory treatments for patients at increased risk of developing cancer due to anti-Neu5Gc-Tn antibodies.

O-linked glycosylation is incomplete in cancer because somatic Cosmc mutations on the X chromosome results in expression of sialylated Tn (STn) antigen in cancer, particularly carcinomas. In one embodiment, the invention provides methods and compositions that embody the discovery that incorporation of dietary Neu5Gc in cancer results in conversion of a portion of the STn into Neu5Gc-Sialyl Tn (GcSTn). In another embodiment, the invention provides methods and compositions that embody the discovery that the immune system sees the GcSTn as foreign and generates antibodies against it, which can be detected, using the invention's compositions and methods, in the subject's tissue, including in serum. In another embodiment, the invention provides methods and compositions that embody the discovery that these antibodies against GcSTn show improved sensitivity and specificity for cancer versus normal serum, as compared to prior art cancer markers. Thus, in a further embodiment, the invention provides methods and compositions that embody the discovery that measuring an increase in the level of these may be used for the early detection of a variety of cancers, particularly carcinomas.

In particular embodiments, the invention provides methods and compositions for detecting human antibodies (including circulating antibodies) induced against the non-human disaccharide N-glycolylneuraminic acid-alpha2-6-N-acetylgalactosamine-alpha-OR (Neu5Gcα2-6-GalNAcα-OR; Neu5Gc-sialyl-Tn, hereafter called "Gc-STn") for the diagnosis of cancer, cancer risk and vaccination/tolerization effect. Neu5Gc is not made in humans, but is present in large amounts in the diet (specifically in red meat and diary) and is preferentially taken up by cancerous and pre-cancerous cells, via pinocytosis and a sialic-acid lysosomal transporter, which are upregulated in cancer. Cancer cells also frequently undergo a hemizygous loss of the X-linked gene COSMC, leading to production of the tumor marker sialyl-Tn. The combination of sialyl-Tn and dietary Neu5Gc incorporation generated the invention's novel xenoautoantigen Neu5Gc-sialylated antigens (e.g., Gc-STn). The human immune system sees the invention's Neu5Gc-sialylated antigens (e.g., Gc-STn) as foreign and generates an antibody response against it. Individuals with inappropriately elevated levels of antibodies against the invention's Neu5Gc-sialylated antigens (e.g., Gc-STn) thus have an increased risk of cancer because the immune system is detecting the presence of the xenoautoantigen in occult cancerous cells. Changes in the levels of these antibodies can be used to screen for the development and/or progression of cancer. This invention can also be used to monitor the effect of vaccination/tolerization for cancer prevention using the invention's Neu5Gc-sialylated antigens (e.g., Gc-STn) as an antigen.

In addition to sialyl-Tn, embodiments of the invention include other cancer-associated sialosides including, but not limited to, sialyl-Le$^x$ (Neu5Acα2-3Galβ1-4(Fucα1-3)GlcNAc) and its regioisomer sialyl-Le$^a$ (Neu5Acα2-3Galβ1-3(Fucα1-4)GlcNAc; and 9-O-acetyl-G$_{D3}$ (Neu-5,9Ac$_2$α2-8Neu5Acα2-3Galβ1-4Glcβ1-1Ceramide). Neu5Gc can also replace Neu5Ac in other tumor-associated glycan structures, thereby generating other novel biomarkers, e.g. Gc-sialyl-Le$^x$.

While most biomarker discovery strategies are based on a global comparative search of cancer versus controls, we chose a hypothesis-driven biomarker approach based on our surprising findings regarding anti-Neu5Gc antibodies. Data herein demonstrate that consumption of dietary Neu5Gc, especially by cancer patients, results in replacement of Neu5Ac by Neu5Gc, generating novel xeno-auto-antigens, with corresponding specific xeno-auto-antibodies that are useful as biomarkers for, for example, early screening of carcinomas.

Data herein provides the exemplary xeno-auto-antigen Neu5Gcα2-6GalNAcα1-O-Ser/Thr (GcSTn) that is specifically detected by the human humoral immune system. Data using a glycan array with 20 pairs of Neu5Gc and Neu5Ac glycans (differing by a single oxygen atom) show that antibodies against GcSTn have the promising ability to distinguish patients with carcinomas (and in particular, non-metastatic carcinomas) compared to healthy controls. Such xeno-auto-antibodies have potential for diagnostic and prognostic approaches to human cancers.

A high-throughput sialoglycan-microarray was printed with 20 of the possible Neu5Gc-containing structures and their corresponding Neu5Ac-matched glycans as controls. Sera from patients with breast carcinoma or other carcinomas and sera from healthy controls were overlaid on the glycan-arrays, and the antibodies bound to each glycan assayed. Samples were split into training and validation data sets for the statistical analysis. Here we show that while anti-Neu5Gc antibodies with various specificities are prevalent in human sera, only anti-Neu5Gc-Sialyl-Tn antibodies are consistently elevated in carcinoma patients compared to healthy controls.

Data herein demonstrate the surprising finding that consumption of dietary Neu5Gc, especially by cancer patients, results in replacement of Neu5Ac by Neu5Gc, generating novel xeno-auto-antigens. Specifically, when the terminal Neu5Ac in the cell surface glycan marker Sialyl-Tn (Neu5Acα2-6GalNAcα1-O-Ser/Thr) is replaced by Neu5Gc, this leads to the generation of the novel xeno-auto-antigen Neu5Gcα2-6GalNAcα1-O-Ser/Thr (GcSTn), along with its corresponding specific xeno-auto-antibodies, anti-Neu5Gc-STn antibodies (FIG. 3D). Here we demonstrate that antibodies against this novel xeno-auto-antigen, anti-Neu5Gc-STn antibodies, could be used as novel biomarkers for early screening of carcinomas. This was discovered in an un-biased glycan microarray approach on relatively large sample size of human sera that allowed us to use stringent statistical analysis (Hawkins, 2004, Ransohoff, 2004).

In some embodiment, the invention's compositions (e.g., Neu5Gc-sialylated antigens, Neu5Gc-sialylated glycans, etc.) are immobilized on a solid surface (e.g., on a bead or array) (See U.S. Pat. Publication No. 2010/0075344). In a preferred embodiment, the invention's glycan is bound to a support that optimally exposes the three-dimensional glycan structure on the array or bead surface. Methods for preparing glycan arrays are described in PCT/US2005/007370 filed Mar. 7, 2005, U.S. Provisional Patent Application No. 60/629,666 filed Nov. 19, 2004, each incorporated herein by this reference in their entirety and made a part of this specification. Linking systems have been described in U.S. Provisional Patent Application No. 60/833,249 filed Jul. 26, 2006, incorporated herein by this reference in its entirety and made a part of this specification.

EXPERIMENTAL

The following examples serve to illustrate certain embodiments and aspects of the present invention and are not to be construed as limiting the scope thereof.

Example 1

Materials and Methods

Serum Samples.

A total of 386 cancer cases and control human sera were studied, with approval from the Institutional Review Board of the University of California, San Diego. Written, informed consent was obtained in advance. Sera were collected from patients seen at the Moore's UCSD Cancer Center Clinic who did not have known or suspected pregnancy or infection. De-identified serum was placed into 12 separate bar-coded aliquots and stored at −80° C. EDRN common data elements (CDE) related to sample handling were captured prospectively and recorded in the Biorepository database. We tested sera from 175 breast cancer patients and other types of carcinomas including prostate (39), ovary (29), lung (14), colon (22), pancreas (16), endometrium (11), as well as controls (80) matched for gender and, as possible, for age. Control sera were obtained from patients seen at the Cancer Center clinics who do not have a diagnosed cancer, including those with benign tumors, therefore raising the bar, as it makes it even more difficult to distinguish between cancer and control (there were 13 benign tumor subjects in the control group including 3 parathyroid, 3 skin, 2 ovary, 2 thyroid, 1 adrenal, 1 breast, and 1 oropharynx). Across all the cancer cases, there were a total of 66 patients with metastatic disease (34 breast cancer, 5 prostate, 3 ovary, 8 lung, 7 colon, 9 pancreas, 0 endometrium). Sera samples for analysis were divided between two separate facilities with 10 samples overlapped for quality control. De-identified serum specimens from Biorepository subjects were subjected to microarray hybridization according to the optimized protocol. Raw data was provided to the biostatistics core for analysis. Thus, both the microarray assay and the initial statistical analysis were conducted blinded to the case/control status of the samples.

Antibodies.

Purified human Immunoglobulins (IgG), Cy5- or Cy3-streptavidin, Cy3-goat-anti-human IgG (H+L), Cy5- or Cy3-AffiniPure donkey-anti-chicken IgY (IgG)(H+L), HRP-conjugated goat-anti-human Fc fragment and HRP-conjugated goat-anti-mouse Fc fragment were from Jackson ImmunoResearch Laboratories, and affinity purified chicken anti-Neu5Gc as prepared as described (4).

Glycoconjugates.

All polyacrylamide (PAA)-glycoconjugates were from GlycoTech. Human serum albumin (HSA)-conjugated sialosides were synthesized as described (6, 7). Sialoglycans pairs (in which the only difference is Neu5Ac versus Neu5Gc) were synthesized using an efficient one-pot three-enzyme chemoenzymatic synthetic system, as previously described (8-10). The sialic acid (Sia) content of all the glycoconjugates used was analyzed for their type (NeuAc/Neu5Gc+/−O-acetylation), quantity and purity. Sias were released from glycoconjugates by acid hydrolysis using 2 M acetic acid followed by hydrolysis for 3 hours at 80° C. Free Sias were then derivatized with 1,2-diamino-4,5-methylenedioxybenzene (DMB) and analyzed with fluorescence detection by reverse-phase HPLC (DMB-HPLC). Quantification of Sias was done by comparison with known quantities of DMB-derivatized Neu5Ac (11).

Sialoglycan-Microarray Fabrication.

Epoxide-derivatized Corning slides were purchased from Thermo Fisher Scientific (Pittsburgh, Pa.) and the arrays were printed with SMT-S50, Classic silicon pins with 50×50 μm tips from Parallel Synthesis Technologies (Santa Clara, Calif.) using a UCSF DeRisi Linear Servo Motor Microarrayer, generating ~70 μm diameter spots. 40 glycoconjugates (Table 2) were distributed into a 384-well source plate using 4 replicate wells per sample and 5 μl per well (Version 7). Each glycoconjugate was prepared at four concentrations of 250, 125, 62.5 and 12.5 μM in an optimized print buffer (300 mM phosphate buffer, pH 8.4). To monitor printing quality we used replicate-wells of human IgG (Jackson ImmunoResearch) at 150 μg/ml (in PBS) for each printing-pin. 16 pins were used, with each pin printing 4 replicate spots/well (by using the 384-well source plate 4 times), 20 spots/row with spacing of 220 mm. One complete array was printed on each slide (within approximately 1 hour/~200 slides). The humidity level in the arraying room was maintained at about 70% during printing. Printed slides were left on arrayer deck overnight, allowing humidity to drop to ambient levels. Next, the print order of the slides was recorded (using Fine Tip Black lab marker from VWR) and slides were packed, vacuum-sealed and stored in a desiccant chamber at RT until used. Slides were printed over 12 days in four batches of ~200 slides each, from two 384-well source plates (one plate for each two print batches) that were developed within one month. Sera binding to array slides was tested and analyzed as detailed herein.

20 Sialoglycans pairs (Neu5Ac versus Neu5Gc; Table 2) were synthesized as described (27-29) and printed on Epoxide slides (Thermo Fisher Scientific, Corning, Pittsburgh, Pa.) in 250, 125, 62.5 and 12.5 μM at 4 replicates each in an optimized print buffer (300 mM phosphate buffer, pH 8.4), and sera binding to arrays tested and analyzed as detailed herein.

Serum-Binding Assays.

Slides were incubated for 1 hour in a staining dish with 50° C. pre-warmed blocking solution (0.05 M Ethanolamine in 0.1 M Tris pH 9) to block the remaining reactive groups on the slide surface, then washed twice with 50° C. pre-warmed dH2O, Slides were placed in Antibody Amplifier ProHisto (Columbia, S.C.) and blocked with 5 ml/slide blocking solution 2 (PBS/OVA, 1% w/v Ovalbumin in PBS pH 7.4) for 1 hour at room temperature (RT), with gentle shaking. Next, the blocking solution was aspirated and 1:100 diluted serum samples were added to each slide (in PBS/OVA, 2.5 ml/slide) and allowed to incubate with gentle shaking for 2 h at RT. Slides were washed twice with PBST (PBS, 1% Tween) then with PBS for 10 min/wash with shaking. Bound antibodies were detected by incubating with Cy3-goat-anti-human IgG (H+L) (Jackson ImmunoResearch) diluted 1:500 in PBS (1.5 mg/ml) at RT for 1 hour. Slides were washed twice with PBST (PBS, 1% Tween) then with PBS followed by $dH_2O$ for 10 min/wash with shaking, then centrifuged at 200×g for 3 min Dry slides were vacuum-sealed and stored in dark until scanning the following day.

Array Slide Processing.

Slides from 4 print days were used (day 1:198 slides; day 2:118 slides; day 3:150; and day 4:2). Slide assays were performed in parallel at two facilities according to the distribution of human sera samples. Statistical analysis conducted to compare reproducibility between facilities and showed they were very comparable in detecting elevated Neu5Gc glycan antibody expression levels. Slides were developed simultaneously by both facilities on a total of 10 different days (within a month after printing), while blinded to case/control status of the samples being assayed. Slides were scanned one day after development (max 48 slides/day) at two gains (to avoid loss of marginal high/low signals), as described below. For quality control (QC) in each experimental day three control slides were assayed along with the sera samples. This included Cy3-anti-human IgG antibody (1:500, 1.5 μg/ml) as a singular detector on a slide, human serum with known high reactivity to multiple Neu5Gc-glycan epitopes (1:100; S34 as described (7)) detected with Cy3-anti-human IgG antibody, and with a polyclonal affinity purified chicken anti-Neu5Gc antibody (1:10,000) (4) detected with Cy3-AffiniPure donkey-anti-chicken IgY (1:1,000, 0.75 μg/ml), as detailed in the main text. If we use glycan 6 as a representative (thus there are 16 values per slide: 4 replicate titration curves with concentrations 12.5, 62.5, 125, 250 μM), the log antibody expression values at gain=350 from Cy3-anti-human IgG were consistently low and with little variability (11 slides; Q1 range: 5.70-5.70; median range: 5.70-5.71; Q3 range: 5.70-5.75), whereas the values from the polyclonal chicken anti-Neu5Gc antibody (10 slides; Q1 range: 5.71-7.15; median range: 6.80-7.53; Q3 range: 7.0-7.68) were consistently high, and the values from S34 (11 slides; Q1 range: 5.70-7.28; median range: 6.09-7.69; Q3 range: 6.33-7.81) were more variable. These 32 control slides were made on 11 scan dates, 5 print days and with 5 different slide print numbers.

Image Processing.

Slides were scanned at 10 μm resolution with a Genepix 4000B microarray scanner (Molecular Devices Corporation, Union City, Calif.) using two gains (350 and 450). Image analysis was carried out with Genepix Pro 6.0 analysis software (Molecular Devices Corporation). Quality checking and image analysis procedures were determined using an initial training data set of 5 cases and 5 controls. Spots were defined as circular features with a fixed radius of 100 μm; this gave more consistent results than the variable radius feature in the Genepix scanning software. Local background subtraction was performed and the differences were shifted up by a relatively small constant (visually chosen to be 300 based on the plots for the raw data) to eliminate negative values; the shifted differences were set to be 100 if they are <100 units; and all values were log-transformed to ensure normality. Results using the two gains were consistent; data from gain 350 were used in the final analysis.

Subject Characteristics.

A total of 386 cancer cases and controls were involved in this study as described in Table 1. Across all the cancer cases, there were a total of 66 cases with metastatic disease. To develop a primary analysis plan and train the initial classifier, 5 breast cancer cases and 5 controls with un-blinded case/control status were used. The validation data for the initial classifier included 175 breast cancer subjects and 50 controls with case/control status blinded to both the analyzing statisticians and scientists who assayed the sera. The case/control status for these subjects was then un-blinded to the senior author only and half of the previous samples (87 cancer subjects and 25 controls) were randomly selected as a training set to select glycans for further consideration. The other half (86 cancer subjects and 25 controls) were used as a second validation set to which the statisticians remained blinded at this stage. A final independent validation set included 131 cases from other cancer types and 30 additional controls.

Array Statistical Methods.

We initially used 24 slides hybridized with human serum with known high anti-Neu5Gc antibodies (S34 as previously described (Padler-Karavani et al., 2008)) to develop quality control and analysis methods. Subsequently, a small training set of 5 breast cancer cases and 5 controls were used to develop our quantitative assessment of Neu5Gc antibody response and to train our initial classifier.

Data were plotted separately for each subject-slide with different symbols used for different pin-blocks or concentrations; we used antibody expression values after background subtraction, shifting and thresholding and log transformation as described above. Expression values of antibodies against the 20 Neu5Ac glycans remained consistently low across subjects, and so the average Neu5Ac antibody expression within each slide was taken as a normalizing factor. Each subject's anti-Neu5Gc antibody response on a slide was summarized with two parameters (intercept α and slope β), which describe anti-Neu5Gc antibody response as a function of Neu5Gc glycan concentration. These parameters were estimated from a mixed-effects model fit to the data for each subject. In the model we initially included random effects for all potential major sources of variation (printing day, scanning day, slide print number and pin-block number), however we retained only effects consistently significant across subjects, using a likelihood ratio test at 10% significance level. The final model used to derive the parameters α (mean difference between Neu5Gc and Neu5Ac glycans at the lowest concentration) and β (difference in slopes between Neu5Gc and Neu5Ac glycans as the concentration increases) for each subject is detailed below. This model included an indicator for Neu5Gc (1 for Neu5Gc and 0 for Neu5Ac), a term for concentration (values 0, 1, 2, and 3 corresponded with four concentrations 12.5, 62.5, 125, and 250 μM, respectively) and the interaction term of the Neu5Gc indicator with concentration; a random block effect was included to account for the variation between the pin-blocks (there are usually 16 blocks within each slide; a slide corresponds to one subject):

$$y_{ijk} = \alpha_0 + \alpha * I_i(Gc) + \beta_0 * \text{concentration}_j + \beta * I_i(Gc) * \text{concentration}_j + \text{random}(\text{block}) + \text{error}_{ijk}$$

$y_{ijk}$ is the transformed antibody expression value;
i=1, ..., 20 (indexes 20 Neu5Ac glycans) and 21 (indexes each of the 4 Neu5Gc glycan of interest).
j=1, 2, 3, and 4, which indexes the four concentration values tested, respectively;
k=1, 2, 3, and 4, which indexes the four replicates (of each glycan in each concentration).

For both the training and two validation data sets, for each glycan, parameters α and β were obtained for each subject as the measure of anti-Neu5Gc antibody response and were then used as predictors in a logistic regression model to discriminate between cancer cases and controls. The predictive power of the regression was assessed using the area-under-the-curve (AUC) of the ROC curve, and 10-fold cross-validation (cv) was used assess to the variability of the ROC curves. In each cv run, 90% of the cases and 90% of the controls in a data set were randomly selected, and estimated coefficients from the fitted logistic regression were then obtained to calculate the probability for a subject being a case in the remaining 10% of subjects. An AUC was calculated for each run and mean AUC was then calculated across all the 500 runs. The 2.5th and 97.5th percentiles were used to construct the 95% confidence intervals on the AUC's. Summary ROC curves were plotted; ROC curves were horizontally averaged to calculate specificities at a given sensitivity level. Analyses were performed in R version 2.5; the ROCR package (12) was used to summarize the cross-validated ROC curves.

Example 2

In an exemplary embodiment, we used a unique sialoglycan-microarray to describe antibodies against a diet-related antigen as novel type of human serum carcinoma-biomarker. This establishes the new concept that a diet-derived antigen can metabolically-incorporate into tumors, generating a novel antigen detected by the immune system.

TABLE 1

Review of the studied subjects, by cancer type.

| Case/Control | | Number of subjects | Number of subjects excluding metastatic cancers |
|---|---|---|---|
| Type of cancer | Breast | 175 | 141 |
| | Prostate | 39 | 34 |
| | Ovary | 29 | 26 |
| | Lung | 14 | 6 |
| | Colon | 22 | 15 |
| | Pancreatic | 16 | 7 |
| | Endometrial | 11 | 11 |
| Total cases | | 306 | 240 |
| Controls | | 80 | 80 |
| Total Cases + Controls | | 386 | 320 |

TABLE 2

List of Glycans Studied on the Array.

| Glycan Type | O-Acetylation Status | Glycan No. | Compound |
|---|---|---|---|
| Ac | 9OAc | 1 | Neu5,9Ac$_2$α2-3Galβ1-4GlcNAcβProNH$_2$ |
| Gc | 9OAc | 2 | Neu5Gc9Acα2-3Galβ1-4GlcNAcβProNH$_2$ |
| Ac | 9OAc | 3 | Neu5,9Ac$_2$α2-6Galβ1-4GlcNAcβProNH$_2$ |
| Gc | 9OAc | 4 | Neu5Gc9Acα2-6Galβ1-4GlcNAcβProNH$_2$ |
| Ac | — | 5 | Neu5Acα2-6GalNAcαProNH$_2$ |
| Gc | — | 6 | Neu5Gcα2-6GalNAcαProNH$_2$ |
| Ac | 9OAc | 7 | Neu5,9Ac$_2$α2-3-Galβ1-3GlcNAcβProNH$_2$ |
| Gc | 9OAc | 8 | Neu5Gc9Acα2-3Galβ1-3GlcNAcβProNH$_2$ |
| Ac | 9OAc | 9 | Neu5,9Ac$_2$α2-3Galβ1-3GalNAcαProNH$_2$ |
| Gc | 9OAc | 10 | Neu5Gc9Acα2-3Galβ1-3GalNAcαProNH$_2$ |
| Ac | — | 11 | Neu5Acα2-3Galβ1-4GlcNAcβProNH$_2$ |
| Gc | — | 12 | Neu5Gcα2-3Galβ1-4GlcNAcβProNH$_2$ |
| Ac | — | 13 | Neu5Acα2-3Galβ1-3GlcNAcβProNH$_2$ |
| Gc | — | 14 | Neu5Gcα2-3Galβ1-3GlcNAcβProNH$_2$ |
| Ac | — | 15 | Neu5Acα2-3Galβ1-3GalNAcαProNH$_2$ |
| Gc | — | 16 | Neu5Gcα2-3Galβ1-3GalNAcαProNH$_2$ |
| Ac | — | 17 | Neu5Acα2-6Galβ1-4GlcNAcβProNH$_2$ |
| Gc | — | 18 | Neu5Gcα2-6Galβ1-4GlcNAcβProNH$_2$ |
| Ac | — | 19 | Neu5Acα2-6Galβ1-4GlcβProNH$_2$ |
| Gc | — | 20 | Neu5Gcα2-6Galβ1-4GlcβProNH$_2$ |
| Ac | — | 21 | Neu5Acα2-3Galβ1-4GlcβProNH$_2$ |
| Gc | — | 22 | Neu5Gcα2-3Galβ1-4GlcβProNH$_2$ |
| Ac | 9OAc | 23 | Neu5,9Ac$_2$α2-6GalNAcαProNH$_2$ |
| Gc | 9OAc | 24 | Neu5Gc9Acα2-6GalNAcαProNH$_2$ |
| Ac | — | 25 | Neu5Acα2-3GalβProNH$_2$ |
| Gc | — | 26 | Neu5Gcα2-3GalβProNH$_2$ |
| Ac | — | 27 | Neu5Acα2-6GalβProNH$_2$ |
| Gc | — | 28 | Neu5Gcα2-6GalβProNH$_2$ |
| Ac | 9OAc | 29 | Neu5,9Ac$_2$α2-3GalβProNH$_2$ |
| Gc | 9OAc | 30 | Neu5Gc9Acα2-3GalβProNH$_2$ |
| Ac | 9OAc | 31 | Neu5,9Ac$_2$α2-6GalβProNH$_2$ |
| Gc | 9OAc | 32 | Neu5Gc9Acα2-6GalβProNH$_2$ |
| Ac | — | 33 | Neu5Acα2-3Galβ1-3GalNAcβProNH$_2$ |
| Gc | — | 34 | Neu5Gcα2-3Galβ1-3GalNAcβProNH$_2$ |
| Ac | 9OAc | 35 | Neu5,9Ac$_2$α2-3Galβ1-3GalNAcβProNH$_2$ |
| Gc | 9OAc | 36 | Neu5Gcα2-3Galβ1-3GalNAcβProNH$_2$ |
| Ac | 9OAc | 37 | Neu5,9Ac$_2$α2-6Galβ1-4GlcβProNH$_2$ |
| Gc | 9OAc | 38 | Neu5Gc9Acα2-6Galβ1-4GlcβProNH$_2$ |
| Ac | 9OAc | 39 | Neu5,9Ac$_2$α2-3Galβ1-4GlcβProNH$_2$ |
| Gc | 9OAc | 40 | Neu5Gc9Acα2-3Galβ1-4GlcβProNH$_2$ |

Twenty Glycan pairs that differ by a single oxygen atom were synthesized and printed on epoxy-coated slides. Glycan Numbers clustered according to terminal sialic acid: Neu5Ac (Ac: 1-20) and Neu5Gc (Gc: 21-40). Glycans are numbered according to terminal Sia: odd numbers indicate Neu5Ac (Ac) and even numbers are Neu5Gc (Gc). ProNH$_2$=O(CH$_2$)$_2$CH$_2$NH$_2$

TABLE 3

Selection of significant glycans for validation testing.

| | | Cross-validated AUC: training data | |
|---|---|---|---|
| Glycan No. | Compound | Including metastatic cases (87 cases, 25 controls) | Excluding metastatic cases (67 cases, 25 controls) |
| 2 | Neu5Gc9Acα2-3Galβ1-4GlcNAcβProNH$_2$ | 0.63 | 0.62 |
| 4 | Neu5Gc9Acα2-6Galβ1-4GlcNAcβProNH$_2$ | 0.44 | 0.44 |
| 6 | Neu5Gcα2-6GalNAcαProNH$_2$ | 0.64 | 0.63 |

TABLE 3-continued

Selection of significant glycans for validation testing.

| | | Cross-validated AUC: training data | |
|---|---|---|---|
| Glycan No. | Compound | Including metastatic cases (87 cases, 25 controls) | Excluding metastatic cases (67 cases, 25 controls) |
| 8  | Neu5Gc9Acα2-3Galβ1-3GlcNAcβProNH$_2$     | 0.46 | 0.47 |
| 10 | Neu5Gc9Acα2-3Galβ1-3GalNAcαProNH$_2$     | 0.37 | 0.43 |
| 12 | Neu5Gcα2-3Galβ1-4GlcNAcβProNH$_2$        | 0.52 | 0.53 |
| 14 | Neu5Gcα2-3Galβ1-3GlcNAcβProNH$_2$        | 0.53 | 0.54 |
| 16 | Neu5Gcα2-3Galβ1-3GalNAcαProNH$_2$        | 0.54 | 0.55 |
| 18 | Neu5Gcα2-6Galβ1-4GlcNAcβProNH$_2$        | 0.48 | 0.41 |
| 20 | Neu5Gcα2-6LacβProNH$_2$                  | 0.59 | 0.58 |
| 22 | Neu5Gcα2-3Galβ1-4GlcβProNH$_2$           | 0.31 | 0.36 |
| 24 | Neu5Gc9Acα2-6GalNAcαProNH$_2$            | 0.51 | 0.53 |
| 26 | Neu5Gcα2-3GalβProNH$_2$                  | 0.44 | 0.46 |
| 28 | Neu5Gcα2-6GalβProNH$_2$                  | 0.34 | 0.32 |
| 30 | Neu5Gc9Acα2-3GalβProNH$_2$               | 0.54 | 0.55 |
| 32 | Neu5Gc9Acα2-6GalβProNH$_2$               | 0.30 | 0.29 |
| 34 | Neu5Gcα2-3Galβ1-3GalNAcβProNH$_2$        | 0.57 | 0.58 |
| 36 | Neu5Gc9Acα2-3Galβ1-3GalNAcβProNH$_2$     | 0.41 | 0.43 |
| 38 | Neu5Gc9Acα2-6Galβ1-4GlcβProNH$_2$        | 0.54 | 0.53 |
| 40 | Neu5Gc9Acα2-3Galβ1-4GlcβProNH$_2$        | 0.51 | 0.52 |

Glycans with AUC above 0.55 (21, 23, 30, and 37) were selected as the glycans of interest to carry into validation testing, excluding metastatic cases. For each glycan, the two antibody response summary variables α and β, obtained from a mixed-effects model, were used to discriminate cases from controls using logistic regression. Ten-fold cross-validation was used to estimate the AUC: on each run, 11 subjects were randomly selected for cross-validation and the remaining 101 subjects were used to estimate a logistic regression model. Coefficients from the model were used to discriminate cases from controls on the 11 cross-validation subjects and the AUC was recorded. A total of 500 cross-validation runs were made for each of the 20 glycans and the mean AUC from the cross-validation is presented below. ROC curves and corresponding AUC's were calculated for 500 ten-fold cross-validation runs. Glycans with mean AUC above 0.55 (2, 6, 20, and 34) were selected as the glycans of interest to carry into validation. ProNH$_2$=O(CH$_2$)$_2$CH$_2$NH$_2$.

TABLE 4

Summary of predictive ability of 4 exemplary glycans using validation data.

| | Model includes | Mean AUC | |
|---|---|---|---|
| Model | Glycan No. | Training set (n = 92) | Validation set (n = 99) |
| 1 | 2  | 0.62 | 0.46 |
| 2 | 6  | 0.63 | 0.58 |
| 3 | 20 | 0.58 | 0.57 |
| 4 | 34 | 0.58 | 0.51 |

As summarized in Table 2, four glycans (glycans 2, 6, 20 and 34) were carried forward to the independent validation data set (74 non-metastatic breast cancer cases, 25 controls). Two of these glycans (#6 and 20) were validated as having mean AUC's above 0.55, as estimated by cross-validation.

TABLE 5

Summary of predictive ability of glycan 6 according to cancer type in validation data.

| Cancer type | No. of subjects | Glycan 6 Mean AUC |
|---|---|---|
| Prostate    | 34 | 0.567 |
| Ovarian     | 26 | 0.605 |
| Lung        | 6  | 0.615 |
| Colon       | 15 | 0.486 |
| Pancreatic  | 7  | 0.359 |
| Endometrial | 11 | 0.615 |

Example 3

Results: Evaluation and Optimization of Sialoglycan-Microarray for Biomarker Discovery: Array Sensitivity Analysis and Validation A microarray approach permits high-throughput analysis of multiple samples and is valuable for comparative human serum profiling (33). To screen multiple anti-Neu5Gc IgGs in human sera, we used a highly efficient chemoenzymatic approach (27-29) to synthesize 40 sialylated glycans representing potentially common sialyloglycans on tumor cells. These 20 matched sialoglycan-pairs terminated with Neu5Gc or Neu5Ac, (Table 2; differing by one oxygen atom) and some of their 9-O-acetylated forms, were printed on Epoxy-coated slides in a range of concentrations. Slide print quality was monitored with polyclonal affinity-purified chicken anti-Neu5Gc IgY (34), and with a positive control human serum, both showing specific high reactivity to multiple Neu5Gc-glycans but not Neu5Ac-glycans. Next, sera from cancer or non-cancer patients were tested on the sialoglycan-microarray, and the potential of anti-Neu5Gc IgGs as cancer-biomarkers assessed.

To determine whether circulating anti-Neu5Gc antibodies, recognizing a variety of Neu5Gc-containing epitopes, or at least some of them, might be used as predictors of cancer, a multiplexed approach was needed to assess the profile of the various anti-Neu5Gc antibodies in cancer patients versus control sera. A microarray approach permits concurrent analysis of multiple samples in a relatively short time with minimal materials, and is valuable for comparative human serum profiling, especially when many targets are screened. Yet this technology is also prone to variability that should be evaluated and addressed properly and minimized through optimization (Li et al., 2009, Liu et al., 2009, Oyelaran et al., 2009).

To screen the variety of anti-Neu5Gc antibodies in multiple human sera, we used an efficient one-pot three-enzyme chemoenzymatic synthetic system (Wu et al., 2004, Yu et al., 2006, Yu et al., 2007, Padler-Karavani et al., 2008) to chemically synthesize 40 sialylated glycans representing the most common terminal sialylated structures that might occur on tumor cells. These glycans were terminated with either Neu5Gc or Neu5Ac, giving 20 matched glycan-pairs (Table 2) that differ by only one oxygen atom. In addition, each glycan contained a spacer with a primary amino group at the reducing end, designed to allow covalent immobilization to Epoxy-coated slides. Each glycan was first analyzed by DMB-HPLC for purity and exact concentration, then printed with optimized conditions at four concentrations of 250, 125, 62.5 and 12.5 μM with 4 replicates each i.e., 16 spots/glycan, allowing a dynamic range for signal detection. In addition, human IgG was spotted to control for printing and developing conditions of each slide.

Three different reagents were used to monitor slide quality control (QC). First, we used fluorescently labeled anti-human IgG antibody as a singular detector on a slide to monitor control spots printing (detects human-IgG and none of the glycans), allowing us to monitor general variability in the overall printing conditions. Second, we used a polyclonal affinity purified chicken anti-Neu5Gc antibody that is highly specific to all Neu5Gc but not Neu5Ac glycans, as shown in FIG. 1A (Diaz et al., 2009). Last, we used a representative human serum with known high reactivity to multiple Neu5Gc-glycan epitopes and low reactivity with Neu5Ac-glycan epitopes, as shown in FIG. 1B (serum S34 as previously described (Padler-Karavani et al., 2008)).

Example 4

Results: Training an Initial Classifier, Using the Number Glycans with Significantly Expressed Anti-Neu5Gc Antibodies for Each Subject We initially used 24 slides hybridized with human serum with known high anti-Neu5Gc antibodies (S34 as described (7)) to develop quality control and analysis methods. Subsequently, to assess a possible cancer-biomarker in the form of specific anti-Neu5Gc antibodies, we generated a glycan-microarray containing multiple Neu5Gc-epitopes together with their respective Neu5Ac, as a control. Serum samples from cancer or control patients were tested. We used an initial small set of training-data, (5 cancer cases and 5 controls) to train a classifier using the number of significantly elevated anti-Neu5Gc antibodies within each subject, compared to the pan antibody level of 20 Neu5Ac glycans. Anti-Neu5Gc antibodies were considered significantly expressed if the likelihood ratio test p-value for its summary parameters $\alpha$ and $\beta$ differed significantly from 0 at the 0.0025 level (Bonferroni adjustment of a significance level of 0.05, adjusted for the 20 Neu5Gc glycans tested). The data suggested a median number of 10 significant comparisons to be used as a cut-off to classify subjects into cases and controls. Results from the two gains gave very similar results: the false positive rate and the false negative rate were both 1/5=20%.

Example 5

Results: Validation of the Initial Classifier Using 225 New Breast Cancer Cases/Controls A total of 175 breast cancer cases and 50 controls with blinded case/control status were analyzed according to the classification rule developed on the initial training data. This analysis was pre-specified and formalized in a memorandum between the primary authors prior to receiving the data: for each subject, the summary parameters $\alpha$ and $\beta$ were derived for each anti-Neu5Gc antibody as before, and if 10 or more of the 20 anti-Neu5Gc antibodies tested were significantly expressed, the subject was to be classified as a case; otherwise the subject was to be classified as a control. Among 225 subjects, 49 (21.8%) were classified as cases and 176 (78.2%) as controls. Calculation done by a third party showed that the sensitivity was 37/175=21.1% and the specificity was 34/50=68%. The statistical team remained blinded as to the case control status of these subjects throughout this analysis.

A similar pre-specified secondary analysis was performed to use specific sub-groups of the Neu5Gc glycans, selected according to the linkage to the underlying glycan ($\alpha$2-3 or $\alpha$2-6) or according to the Sia O-Acetylation status, to compare to the pan Neu5Ac level. The median number of comparisons was also used as a cut-off for cases vs. controls. There was no noted improvement in increasing sensitivity or specificity.

Example 6

Results: Training a Second Classifier Using the Response Level of Each Anti-Neu5Gc Antibody Training a Classifier for Cancer Versus Control Status.

We developed a classifier to distinguish cancer cases from controls using the sialoglycan-microarray. Such a classifier is a rule to call a subject as a case or control, using output from the sialoglycan-microarray assay of the subjects' serum. We used an initial training set of 5 cases and 5 controls to develop our data standardization and filtering protocols, and to develop summary measures for each subject's antibody response. An initial classifier trained on these preliminary data used the number of Neu5Gc-glycans (out of 20) with significantly elevated anti-Neu5Gc IgG signals for each subject, and resulted in limited sensitivity and specificity. Subsequently, each subject's anti-Neu5Gc IgG responses on a slide were summarized with two parameters (intercept $\alpha$ and slope $\beta$), which describe anti-Neu5Gc IgG response as a function of Neu5Gc glycan concentration. We tested whether using this more detailed measure of response to each glycan ($\alpha$ and $\beta$) could improve sensitivity and specificity. Half of the breast cancer cases and female controls with no cancer were randomly selected from 225 subjects to form the training data (Table 1; 112 breast cancer cases, including 67 non-metastatic cases and 50 controls). These data were used to screen the 20 glycans for predictive power, and the statistical team remained blinded to the selection. The case/control status was then un-blinded and parameters $\alpha$ and $\beta$ from each subject were used as training data for a classifier. The 20 glycans were initially screened singly for discriminatory power and ten-fold cross-validation was used to estimate the AUC (area under the receiver operator characteristic (ROC) curve) for each glycan (Table 3). A ROC curve plots the true-positive rate against the false-positive rate for the different possible cut-points of a diagnostic test. The area under the curve (AUC) measures discrimination, that is, the ability of the test to correctly classify those with and without disease. Multivariate models did not improve on univariate results; however, removing metastatic cases from the analysis slightly improved most classification results (Table 3), possibly due to absorption of anti-Neu5Gc antibodies by tumor cells upon elevated tumor burden. Glycans with mean AUC above 0.55 were selected for further validation testing (glycans 2, 6, 20, and 34).

Example 7

Results: Validation of the Second Classifier Using Independent Breast Cancer Cases and Controls The validation data consisted of 74 new non-metastatic breast cancer cases and 25 new controls. The analysis plan was formalized prior to data delivery to the statistical team. Glycans 2, 6, 20, and 34 were assessed for significance as above, using cross-validation mean AUC as a measure of predictive power. We were able to independently replicate our results for two of the 4 glycans (6 and 20), as having estimated mean cross-validated AUC's above 0.55 in these independent data (Table 4). Multivariate models (when all possible combinations of the 4 glycans were tested; 15 models in total) did not improve on univariate results, and the two final best models were those using glycans 6 and 20 alone. However, the multivariate models with the highest mean AUCs all included glycan 6; therefore, the classifier built using glycan 6 alone was considered to be the most promising candidate for further analysis.

Figure 3:
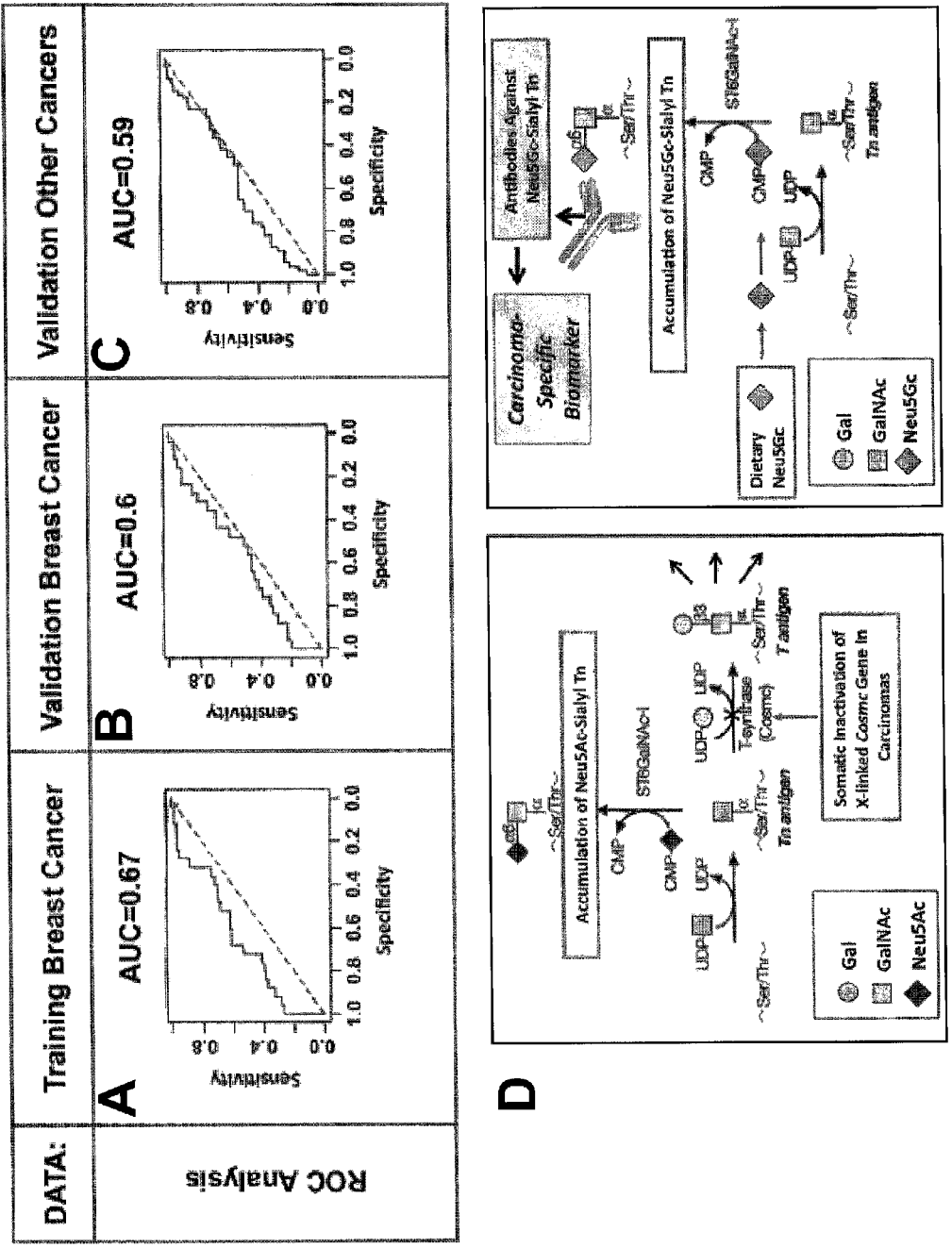
FIG. 3. Anti-GcSTn is a classifier for cancer cases/controls and is suggested to be a human-specific and tumor-associated carcinoma biomarker. Probabilities of being a cancer case were calculated using logistic regression where predictors were the two parameters, $\alpha$ and $\beta$, which summarized the anti-Neu5Gc antibody response to glycan 6 (Neu5Gc-sialyl-Tn; GcSTn) against the pan antibody level of 20 Neu5Ac glycans. (A) ROC curve for training data, used to select glycan 6, that had 67 non-metastatic breast cancer cases and 25 controls. (B) ROC curve for the first validation data set, which had 74 new non-metastatic breast cancer cases and 25 new controls. (C) ROC curve for a second validation data set, which had 99 cases of other cancer types and 55 controls. The biochemical and genetic rationale for the generation of the novel human carcinoma biomarker is schematically presented. (D) Somatic Cosmc mutations generate incomplete O-linked glycosylation, resulting in tumor-associated expression of the sialylated-Tn antigen in many carcinomas (left panel). Incorporation of dietary-Neu5Gc by such carcinomas generates Neu5Gc-sialyl Tn, detected by the humoral adaptive immune system as foreign, thus generating antibodies against it. Such xeno-auto-antibodies specific for Neu5Gc-sialyl Tn, are shown herein to be novel biomarkers for early screening of carcinomas and/or potential immunotherapeutic tools (right panel).
Figure 4:
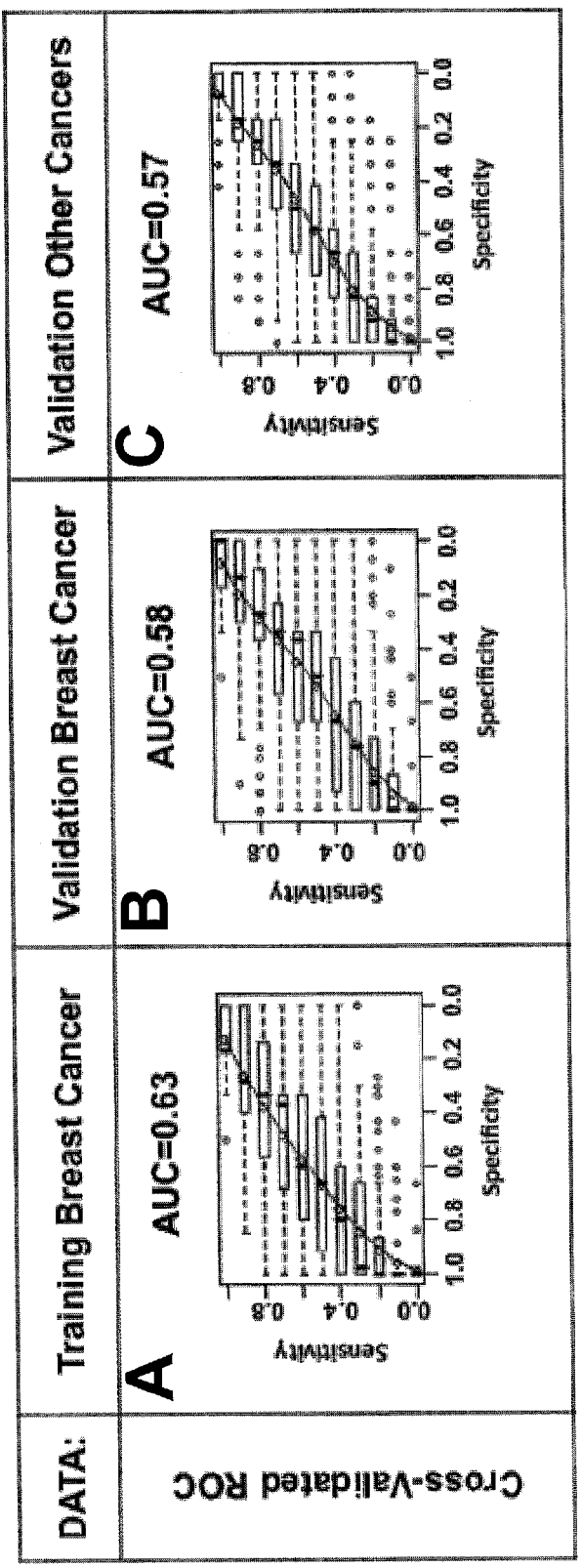
FIG. 4. Cross-validation of ROC analysis of anti-GcSTn as a classifier for cancer cases/controls. Probabilities of being a case were calculated using logistic regression models where predictors were the two parameters, $\alpha$ and $\beta$, which summarized the anti-Neu5Gc antibody response of glycan 6 (Neu5Gc-sialyl-Tn; GcSTn) against the expression levels of 20 Neu5Ac glycans. Ten-fold cross-validation was used to assess the predictive ability. ROC curves were horizontally averaged to calculate specificities at a desired sensitivity level and box plots were made for specificities. (A) ROC curve for training data that had 67 non-metastatic breast cancer cases and 25 controls based on 500 ten-fold cross-validation runs, mean AUC=0.63, 95% CI on AUC=(0.29, 0.91), IQR=(0.46, 0.71). (B) ROC curve for the first validation data set that had 74 new non-metastatic breast cancer cases and 25 new controls based on 500 ten-fold cross-validation runs, mean AUC=0.58, 95% CI on AUC=(0.167, 0.917), IQR=(0.458, 0.708). (C) ROC curve for a second validation data set that had 99 non-metastatic cases of other cancer types and 55 controls based on 500 ten-fold cross-validation runs, mean AUC=0.57, 95% CI on AUC=(0.283, 0.817), IQR=(0.483, 0.683).

As a summary, ROC curves for glycan 6 are presented in FIG. 3, using logistic regression models estimated on training and validation data (results from the cross-validation are given in FIG. 4A-C). For the breast cancer training data (FIG. 3A), which were used to select glycan 6 from among the 20 glycans, using anti-Neu5Gc antibody response as a classifier gave an AUC of 0.67. In the breast cancer validation data, which were used to replicate results, the estimated AUC was 0.60 (FIG. 3B) with a mean AUC of 0.58 after 10-fold cross-validation (FIG. 4B; 95% CI=(0.167, 0.917), IQR=(0.458, 0.708)). These AUC values compare favorably with some common protein-based screens used today for cancer detection (35, 36). In these breast cancer validation data the estimated mean specificity was 0.86 (95% CI=(0.37, 1.00)) at a sensitivity of 0.20 and 0.76 (95% CI=(0.27, 1.00)) at a sensitivity of 0.30, respectively.

Example 8

Results: Independent Validation of Glycan 23 Using Other Types of Carcinoma Cases Versus Controls To further validate the predictive value of glycan 6, we used a second set of independent validation data that included 55 controls (including 25 controls from the breast cancer validation and 30 new controls) and 99 cases with other types of non-metastatic cancer (Table 1). In these data, the estimated AUC was 0.59 (FIG. 3C) with a mean AUC of 0.57 after 10-fold cross-validation (FIG. 4C; 95% CI=(0.283, 0.817), IQR=(0.483, 0.683)). When the sensitivity was 0.2 and 0.3, the estimated mean specificity was 0.89 (95% CI=(0.50, 1.00)) and 0.81 (95% CI=(0.33, 1.00)), respectively (FIG. 4C). Univariate logistic regression of glycan 6 according to cancer type (Table 5) revealed predictive value in carcinomas from prostate, ovarian, lung and endometrium, while it was not correlated with colon and pancreatic cancers, however the number of cases tested in each of these cancers was very small, hence conclusions based on these small size results should be made with caution.

In summary, an unbiased glycan-microarray approach and a relatively large set of human sera allowed stringent statistical analysis to indicate that antibodies to glycan 6 show promise to classify cancer cases from controls with relatively high specificity (true negative), albeit with low sensitivity (true positive).

Example 9

Exemplary Sensitivity and Specificity for Cancer

TABLE 6

Values for anti-GcSTn antibody cancer detection specificity at selected sensitivities

|  | Sensitivity Level | Mean Specificity | Specificity Range |
|---|---|---|---|
| Breast Cancer | 10% | 96.1% | 43.3-100% |
| Training Set | 20% | 91.4% | 20-100% |
|  | 30% | 85.1% | 0-100% |
| Breast Cancer | 10% | 93.9% | 40-100% |
| Validation Set | 20% | 85.9% | 13.3-100% |
|  | 30% | 76.0% | 0-100% |
| Other Cancer | 10% | 95.1% | 33.3-100% |
| Validation Set | 20% | 88.9% | 33.3-100% |
|  | 30% | 81.0% | 16.7-100% |

We used 10-fold cross-validation (CV) to estimate the specificity at a given sensitivity, for each data set. In each CV iteration, 90% of the cases/controls were randomly selected into the CV training set, and CV test set consisted of the remaining 10% of subjects. The coefficients from the fitted logistic regression were then estimated using the CV training set, and the probability of being a case was calculated using these coefficients for each subject in the CV test set. A ROC curve was then computed using the CV test set.

To estimate the specificity at a desired sensitivity, the specificity from the ROC curve at a given sensitivity was averaged over 500 Cross Validation iterations. To be specific, the ROC curve was computed using the R-package (online from "r-project" website) ROCR (online from "rocr.bioinf.mpi-sb.mpg" website in Germany). This algorithm uses linear interpolation to draw the ROC curve from the discrete data. This package was used to draw the ROC curves and box plots in FIG. 3.

The code below was used to generate the cross-validated ROC curves and compute the estimates in the table above:
    plot(perf,avg="horizontal", spread.estimate="boxplot",
        main=main, cex.main=1, sub=aucsummary, xlab='1-Specificity', ylab='Sensitivity')

The following R source code was obtained from the R function .plot.performance, from the R-package ROCR, and used to generate summary values of specificity at given sensitivity levels:

arglist <- list(avg="horizontal", spread.estimate="boxplot")
    arglist <- .farg(arglist, show.spread.at =
    seq(min(unlist(perf@y.values)),
        max(unlist(perf@y.values)), length = 11))
    perf.avg <- perf
    y.values <- seq(min(unlist(perf@y.values)),
    max(unlist(perf@y.values)), -continued

```
        length = max(sapply(perf@y.values, length)))
    for (i in 1:length(perf@x.values)) {
        perf.avg@x.values[[i]] <- approxfun(perf@y.values[[i]],
            perf@x.values[[i]], ties = mean, rule = 2)(y.values)
    }
    perf.avg@x.values <-
    list(rowMeans(data.frame(perf.avg@x.values)))
    perf.avg@y.values <- list(y.values)
    perf.avg@alpha.values <- list( )
    show.spread.at.x.values <- lapply(as.list(1:length(perf@y.values)),
        function(i) {
            approxfun(perf@y.values[[i]], perf@x.values[[i]],
                rule = 2, ties = mean)(.garg(arglist, "show.spread.at"))
        })        show.spread.at.x.values <-
        as.matrix(data.frame(show.spread.at.x.values))
    colnames(show.spread.at.x.values) <- c( )
##sens=.1
round( summary(1-show.spread.at.x.values[2,]),3)
##sens=.2
round( summary(1-show.spread.at.x.values[3,]),3)
##sens=.3
round( summary(1-show.spread.at.x.values[4,]),3)
```

Reference: Technical Report HPL-2003-4 Fawcett, T. (2004) ROC graphs: notes and practical considerations for researchers, Palo Alto, Calif. HP Labs.

REFERENCES (ALPHABETICAL)

An, H. J., Kronewitter, S. R., de Leoz, M. L. and Lebrilla, C. B. (2009) Glycomics and disease markers. *Curr Opin Chem Biol*

Candefjord, S., Ramser, K. and Lindahl, O. A. (2009) Technologies for localization and diagnosis of prostate cancer. *J Med Eng Technol* 33, 585-603

Conze, T., Carvalho, A. S., Landegren, U., Almeida, R., Reis, C. A., David, L. and Soderberg, O. (2009) MUC2 mucin is a major carrier of the cancer-associated sialyl-Tn antigen in intestinal metaplasia and gastric carcinomas. *Glycobiology*

Desmetz, C., Cortijo, C., Mange, A. and Solassol, J. (2009a) Humoral response to cancer as a tool for biomarker discovery. *J Proteomics* 72, 982-988

Desmetz, C., Maudelonde, T., Mange, A. and Solassol, J. (2009b) Identifying autoantibody signatures in cancer: a promising challenge. *Expert Rev Proteomics* 6, 377-386

Diaz, S. L., Padler-Karavani, V., Ghaderi, D., Hurtado-Ziola, N., Yu, H., Chen, X., Brinkman-Van der Linden, E. C., Varki, A. and Varki, N. M. (2009) Sensitive and specific detection of the non-human sialic Acid N-glycolylneuraminic acid in human tissues and biotherapeutic products. *PLoS ONE* 4, e4241

Du, J., Meledeo, M. A., Wang, Z., Khanna, H. S., Paruchuri, V. D. and Yarema, K. J. (2009) Metabolic glycoengineering: sialic acid and beyond. *Glycobiology* 19, 1382-1401

Dube, D. H. and Bertozzi, C. R. (2005) Glycans in cancer and inflammation—potential for therapeutics and diagnostics. *Nat Rev Drug Discov* 4, 477-488

Greene, K. L., Albertsen, P. C., Babaian, R. J., Carter, H. B., Gann, P. H., Han, M., Kuban, D. A., Sartor, A. O., Stanford, J. L., Zietman, A. and Carroll, P. (2009) Prostate specific antigen best practice statement: 2009 update. *J Urol* 182, 2232-2241

Gupta, D. and L is, C. G. (2009) Role of CA125 in predicting ovarian cancer survival—a review of the epidemiological literature. *J Ovarian Res* 2, 13

Hara, S., Yamaguchi, M., Takemori, Y., Nakamura, M. and Ohkura, Y. (1986) Highly sensitive determination of N-acetyl- and N-glycolylneuraminic acids in human serum and urine and rat serum by reversed-phase liquid chromatography with fluorescence detection. *J Chromatogr* 377, 111-119

Hawkins, D. M. (2004) The problem of overfitting. *J Chem Inf Comput Sci* 44, 1-12

Hedlund, M., Padler-Karavani, V., Varki, N. M. and Varki, A. (2008) Evidence for a human-specific mechanism for diet and antibody-mediated inflammation in carcinoma progression. *Proc Natl Acad Sci USA* 105, 18936-18941

Hedlund, M., Tangvoranuntakul, P., Takematsu, H., Long, J. M., Housley, G. D., Kozutsumi, Y., Suzuki, A., Wynshaw-Boris, A., Ryan, A. F., Gallo, R. L., Varki, N. and Varki, A. (2007) N-glycolylneuraminic acid deficiency in mice: implications for human biology and evolution. *Mol Cell Biol* 27, 4340-4346

Johansen, E., Schilling, B., Lerch, M., Niles, R. K., Liu, H., Li, B., Allen, S., Hall, S. C., Witkowska, H. E., Regnier, F. E., Gibson, B. W., Fisher, S. J. and Drake, P. M. (2009) A lectin HPLC method to enrich selectively-glycosylated peptides from complex biological samples. *J Vis Exp*

Ju, T. and Cummings, R. D. (2002) A unique molecular chaperone Cosmc required for activity of the mammalian core 1 beta 3-galactosyltransferase. *Proc Natl Acad Sci USA* 99, 16613-16618

Ju, T., Lanneau, G. S., Gautam, T., Wang, Y., Xia, B., Stowell, S. R., Willard, M. T., Wang, W., Xia, J. Y., Zuna, R. E., Laszik, Z., Benbrook, D. M., Hanigan, M. H. and Cummings, R. D. (2008) Human tumor antigens Tn and sialyl Tn arise from mutations in Cosmc. *Cancer Res* 68, 1636-1646

Kim, Y. J. and Varki, A. (1997) Perspectives on the significance of altered glycosylation of glycoproteins in cancer. *Glycoconj J* 14, 569-576

Kim, Y. S., Yoo, H. S, and Ko, J. H. (2009) Implication of aberrant glycosylation in cancer and use of lectin for cancer biomarker discovery. *Protein Pept Lett* 16, 499-507

Kobata, A. and Amano, J. (2005) Altered glycosylation of proteins produced by malignant cells, and application for the diagnosis and immunotherapy of tumours. *Immunol Cell Biol* 83, 429-439

Li, C., Simeone, D. M., Brenner, D. E., Anderson, M. A., Shedden, K. A., Ruffin, M. T. and Lubman, D. M. (2009) Pancreatic cancer serum detection using a lectin/glycoantibody array method. *J Proteome Res* 8, 483-492

Liu, C. C., Hu, J., Kalakrishnan, M., Huang, H. and Zhou, X. J. (2009) Integrative disease classification based on cross-platform microarray data. *BMC Bioinformatics* 10 Suppl 1, S25

Ludwig, J. A. and Weinstein, J. N. (2005) Biomarkers in cancer staging, prognosis and treatment selection. *Nat Rev Cancer* 5, 845-856

Malykh, Y. N., Schauer, R. and Shaw, L. (2001) N-Glycolylneuraminic acid in human tumours. *Biochimie* 83, 623-634

Marcial, V. A. (1977) Carcinoma of the cervix: present status and future. Cancer 39, 945-958

Martin, L. T., Marth, J. D., Varki, A. and Varki, N. M. (2002) Genetically altered mice with different sialyltransferase deficiencies show tissue-specific alterations in sialylation and sialic acid 9-O-acetylation. *J Biol Chem* 277, 32930-32938

Mechref, Y., Hussein, A., Bekesova, S., Pungpapong, V., Zhang, M., Dobrolecki, L. E., Hickey, R. J., Hammoud, Z. T. and Novotny, M. V. (2009) Quantitative serum glycomics of esophageal adenocarcinoma and other esophageal disease onsets. *J Proteome Res* 8, 2656-2666

Nelson, A. E., Francis, J. E. and Zorbas, H. (2009a) Population screening and early detection of ovarian cancer in asymptomatic women. *Aust N Z J Obstet Gynaecol* 49, 448-450

Nelson, H. D., Tyne, K., Naik, A., Bougatsos, C., Chan, B. K. and Humphrey, L. (2009b) Screening for breast cancer: an update for the U.S. Preventive Services Task Force. *Ann Intern Med* 151, 727-37, W237-42

Nguyen, D. H., Tangvoranuntakul, P. and Varki, A. (2005) Effects of natural human antibodies against a nonhuman sialic acid that metabolically incorporates into activated and malignant immune cells. *J Immunol* 175, 228-236

Nogueira, L., Corradi, R. and Eastham, J. A. (2009) Prostatic specific antigen for prostate cancer detection. *Int Braz J Urol* 35, 521-9; discussion 530-2

Nossov, V., Amneus, M., Su, F., Lang, J., Janco, J. M., Reddy, S. T. and Farias-Eisner, R. (2008) The early detection of ovarian cancer: from traditional methods to proteomics. Can we really do better than serum CA-125? *Am J Obstet Gynecol* 199, 215-223

Oyelaran, O., McShane, L. M., Dodd, L. and Gildersleeve, J. C. (2009) Profiling human serum antibodies with a carbohydrate antigen microarray. *J Proteome Res* 8, 4301-4310

Padler-Karavani, V., Yu, H., Cao, H., Chokhawala, H., Karp, F., Varki, N., Chen, X. and Varki, A. (2008) Diversity in specificity, abundance, and composition of anti-Neu5Gc antibodies in normal humans: potential implications for disease. *Glycobiology* 18, 818-830

Parkin, D. M., Bray, F. I. and Devesa, S. S. (2001) Cancer burden in the year 2000. The global picture. *Eur J Cancer* 37 Suppl 8, 54-66

Raedle, J., Oremek, G., Truschnowitsch, M., Lorenz, M., Roth, W. K., Caspary, W. F. and Zeuzem, S. (1998) Clinical evaluation of autoantibodies to p53 protein in patients with chronic liver disease and hepatocellular carcinoma. *Eur J Cancer* 34, 1198-1203

Ransohoff, D. F. (2004) Rules of evidence for cancer molecular-marker discovery and validation. *Nat Rev Cancer* 4, 309-314

Saldova, R., Wormald, M. R., Dwek, R. A. and Rudd, P. M. (2008) Glycosylation changes on serum glycoproteins in ovarian cancer may contribute to disease pathogenesis. *Dis Markers* 25, 219-232

Sing, T., Sander, O., Beerenwinkel, N. and Lengauer, T. (2005) ROCR: visualizing classifier performance in R. *Bioinformatics* 21, 3940-3941

Soussi, T. (2000) p53 Antibodies in the sera of patients with various types of cancer: a review. *Cancer Res* 60, 1777-1788

Srivastava, S. and Gopal-Srivastava, R. (2002) Biomarkers in cancer screening: a public health perspective. *J Nutr* 132, 2471S-2475S Tan, H. T., Low, J., Lim, S. G. and Chung, M. C. (2009) Serum autoantibodies as biomarkers for early cancer detection. *FEBS J*

Tangvoranuntakul, P., Gagneux, P., Diaz, S., Bardor, M., Varki, N., Varki, A. and Muchmore, E. (2003) Human uptake and incorporation of an immunogenic nonhuman dietary sialic acid. *Proc Natl Acad Sci USA* 100, 12045-12050

Uygur-Bayramicli, O., Dabak, R., Orbay, E., Dolapcioglu, C., Sargin, M., Kilicoglu, G., Guleryuzlu, Y. and Mayadagli, A. (2007) Type 2 diabetes mellitus and CA 19-9 levels. *World J Gastroenterol* 13, 5357-5359 van Leeuwen, P. J., Connolly, D., Gavin, A., Roobol, M. J., Black, A., Bangma, C. H. and Schroder, F. H. (2009) Prostate cancer mortality in screen and clinically detected prostate cancer: Estimating the screening benefit. *Eur J Cancer*

Varki, A. (2001) N-glycolylneuraminic acid deficiency in humans. *Biochimie* 83, 615-622

Varki, A. (2009) Multiple changes in sialic acid biology during human evolution. *Glycoconj J* 26, 231-245

Wu, C. Y., Liang, P. H. and Wong, C. H. (2009) New development of glycan arrays. *Org Biomol Chem* 7, 2247-2254

Wu, X., Ling, C. C. and Bundle, D. R. (2004) A new homobifunctional p-nitro phenyl ester coupling reagent for the preparation of neoglycoproteins. *Org Lett* 6, 4407-4410

Yu, H., Chokhawala, H. A., Huang, S, and Chen, X. (2006) One-pot three-enzyme chemoenzymatic approach to the synthesis of sialosides containing natural and non-natural functionalities. *Nat Protoc* 1, 2485-2492

Yu, H., Chokhawala, H. A., Varki, A. and Chen, X. (2007) Efficient chemoenzymatic synthesis of biotinylated human serum albumin-sialoglycoside conjugates containing O-acetylated sialic acids. *Org Biomol Chem* 5, 2458-2463

Zhang, D. Y., Ye, F., Gao, L., Liu, X., Zhao, X., Che, Y., Wang, H., Wang, L., Wu, J., Song, D., Liu, W., Xu, H., Jiang, B., Zhang, W., Wang, J. and Lee, P. (2009) Proteomics, Pathway Array and Signaling Network-Based Medicine in Cancer. *Cell Div* 4, 20

REFERENCES FOR EXAMPLES 1, 4 AND 5

1. Ghaderi D, Taylor R E, Padler-Karavani V, Diaz S, Varki A. Implications of the presence of N-glycolylneuraminic acid in recombinant therapeutic glycoproteins. Nat. Biotechnol. 2010; 28:863-7.
2. Singer O, Marr R A, Rockenstein E et al. Targeting BACE1 with siRNAs ameliorates Alzheimer disease neuropathology in a transgenic model. Nat. Neurosci. 2005; 8:1343-9.
3. Tiscornia G, Singer O, Verma I M. Production and purification of lentiviral vectors. Nat Protoc. 2006; 1:241-5.
4. Diaz S L, Padler-Karavani V, Ghaderi D et al. Sensitive and specific detection of the non-human sialic Acid N-glycolylneuraminic acid in human tissues and biotherapeutic products. PLoS ONE. 2009; 4:e4241.
5. Kjeldsen T, Clausen H, Hirohashi S, Ogawa T, Iijima H, Hakomori S. Preparation and characterization of monoclonal antibodies directed to the tumor-associated O-linked sialosyl-2----6 alpha-N-acetylgalactosaminyl (sialosyl-Tn) epitope. Cancer Res. 1988; 48:2214-20.
6. Yu H, Chokhawala H A, Varki A, Chen X. Efficient chemoenzymatic synthesis of biotinylated human serum albumin-sialoglycoside conjugates containing O-acetylated sialic acids. Org Biomol Chem. 2007; 5:2458-63.
7. Padler-Karavani V, Yu H, Cao H et al. Diversity in specificity, abundance, and composition of anti-Neu5Gc antibodies in normal humans: potential implications for disease. Glycobiology. 2008; 18:818-30.
8. Yu H, Chokhawala H A, Huang S, Chen X. One-pot three-enzyme chemoenzymatic approach to the synthesis of sialosides containing natural and non-natural functionalities. Nat. Protoc. 2006; 1:2485-92.
9. Yu H, Huang S, Chokhawala H, Sun M, Zheng H, Chen X. Highly efficient chemoenzymatic synthesis of naturally occurring and non-natural alpha-2,6-linked sialosides: a P. damsela alpha-2,6-sialyltransferase with extremely flexible donor-substrate specificity. Angew Chem Int Ed Engl. 2006; 45:3938-44.
10. Yu H, Chokhawala H, Karpel R et al. A multifunctional *Pasteurella multocida* sialyltransferase: a powerful tool for the synthesis of sialoside libraries. J Am Chem. Soc. 2005; 127:17618-9.

11. Hara S, Yamaguchi M, Takemori Y, Nakamura M, Ohkura Y. Highly sensitive determination of N-acetyl- and N-glycolylneuraminic acids in human serum and urine and rat serum by reversed-phase liquid chromatography with fluorescence detection. J. Chromatogr. 1986; 377:111-9.
12. Sing T, Sander O, Beerenwinkel N, Lengauer T. ROCR: visualizing classifier performance in R. Bioinformatics. 2005; 21:3940-1.

ADDITIONAL NUMBERED REFERENCES

1. Varki A, Kannagi R, Toole B P. Glycosylation Changes in Cancer. In: Varki A, Cummings R D, Esko J D, Freeze H H, Stanley P, Bertozzi C R, Hart G W, Etzler M E, editors. Essentials of Glycobiology. Cold Spring Harbor, N.Y.: Cold Spring Harbor Laboratory Press; 2009. p. 617-32.
2. Malykh Y N, Schauer R, Shaw L. N-Glycolylneuraminic acid in human tumours. Biochimie. 2001; 83:623-34.
Tangvoranuntakul P, Gagneux P, Diaz S et al. Human uptake and incorporation of an immunogenic nonhuman dietary sialic acid. Proc Natl Acad Sci USA. 2003; 100:12045-50.
4. Nguyen D H, Tangvoranuntakul P, Varki A. Effects of natural human antibodies against a nonhuman sialic acid that metabolically incorporates into activated and malignant immune cells. J. Immunol. 2005; 175:228-36.
5. Padler-Karavani V, Yu H, Cao H et al. Diversity in specificity, abundance, and composition of anti-Neu5Gc antibodies in normal humans: potential implications for disease. Glycobiology. 2008; 18:818-30.
6. Varki A. Colloquium paper: uniquely human evolution of sialic acid genetics and biology. Proc Natl Acad Sci USA. 2010; 107 Suppl 2:8939-46.
7. Hedlund M, Tangvoranuntakul P, Takematsu H et al. N-glycolylneuraminic acid deficiency in mice: implications for human biology and evolution. Mol Cell Biol. 2007; 27:4340-6.
8. Taylor R E, Gregg C J, Padler-Karavani V et al. Novel mechanism for the generation of human xeno-autoantibodies against the nonhuman sialic acid N-glycolylneuraminic acid. J Exp Med. 2010; 207:1637-46.
9. Hedlund M, Padler-Karavani V, Varki N M, Varki A. Evidence for a human-specific mechanism for diet and antibody-mediated inflammation in carcinoma progression. Proc Natl Acad Sci USA. 2008; 105:18936-41.
10. de Visser K E, Korets L V, Coussens L M. De novo carcinogenesis promoted by chronic inflammation is B lymphocyte dependent. Cancer Cell. 2005; 7:411-23.
11. Andreu P, Johansson M, Affara N I et al. FcRgamma activation regulates inflammation-associated squamous carcinogenesis. Cancer Cell. 2010; 17:121-34.
12. Adams G P, Weiner L M. Monoclonal antibody therapy of cancer. Nat. Biotechnol. 2005; 23:1147-57.
13. Ferris R L, Jaffee E M, Ferrone S. Tumor Antigen-Targeted, Monoclonal Antibody-Based Immunotherapy: Clinical Response, Cellular Immunity, and Immunoescape. J Clin Oncol. 2010
14. Finn O J. Cancer immunology. N Engl J. Med. 2008; 358:2704-15.
15. Prehn R T, Prehn L M. The flip side of immune surveillance: immune dependency. Immunol Rev. 2008; 222:341-56.
16. Marcial V A. Carcinoma of the cervix: present status and future. Cancer. 1977; 39:945-58.
17. Nelson H D, Tyne K, Naik A, Bougatsos C, Chan B K, Humphrey L. Screening for breast cancer: an update for the U.S. Preventive Services Task Force. Ann Intern Med. 2009; 151:727-37, W237-42.
18. Ludwig J A, Weinstein J N. Biomarkers in cancer staging, prognosis and treatment selection. Nat Rev Cancer. 2005; 5:845-56.
19. Gupta D, Lis C G. Role of CA125 in predicting ovarian cancer survival—a review of the epidemiological literature. J Ovarian Res. 2009; 2:13.
20. Schroder F H, Hugosson J, Roobol M J et al. Screening and prostate-cancer mortality in a randomized European study. N Engl J. Med. 2009; 360:1320-8.
21. Tan H T, Low J, Lim S G, Chung M C. Serum autoantibodies as biomarkers for early cancer detection. FEBS J. 2009
22. Soussi T. p53 Antibodies in the sera of patients with various types of cancer: a review. Cancer Res. 2000; 60:1777-88.
23. Drake P M, Cho W, Li B et al. Sweetening the pot: adding glycosylation to the biomarker discovery equation. Clin Chem. 2010; 56:223-36.
24. Singer O, Man R A, Rockenstein E et al. Targeting BACE1 with siRNAs ameliorates Alzheimer disease neuropathology in a transgenic model. Nat. Neurosci. 2005; 8:1343-9.
25. Tiscornia G, Singer O, Verma I M. Production and purification of lentiviral vectors. Nat Protoc. 2006; 1:241-5.
26. Bardor M, Nguyen D H, Diaz S, Varki A. Mechanism of uptake and incorporation of the non-human sialic acid N-glycolylneuraminic acid into human cells. J Biol. Chem. 2005; 280:4228-37.
27. Yu H, Chokhawala H A, Huang S, Chen X. One-pot three-enzyme chemoenzymatic approach to the synthesis of sialosides containing natural and non-natural functionalities. Nat. Protoc. 2006; 1:2485-92.
28. Yu H, Huang S, Chokhawala H, Sun M, Zheng H, Chen X. Highly efficient chemoenzymatic synthesis of naturally occurring and non-natural alpha-2,6-linked sialosides: a P. damsela alpha-2,6-sialyltransferase with extremely flexible donor-substrate specificity. Angew Chem Int Ed Engl. 2006; 45:3938-44.
29. Yu H, Chokhawala H, Karpel R et al. A multifunctional *Pasteurella multocida* sialyltransferase: a powerful tool for the synthesis of sialoside libraries. J Am Chem. Soc. 2005; 127:17618-9.
30. Jolles S, Sewell W A, Misbah S A. Clinical uses of intravenous immunoglobulin. Clin Exp Immunol. 2005; 142:1-11.
31. Oppmann B, Lesley R, Blom B et al. Novel p19 protein engages IL-12p40 to form a cytokine, IL-23, with biological activities similar as well as distinct from IL-12. Immunity. 2000; 13:715-25.
32. Weiss J M, Subleski J J, Wigginton J M, Wiltrout R H. Immunotherapy of cancer by IL-12-based cytokine combinations. Expert Opin Biol Ther. 2007; 7:1705-21.
33. Oyelaran O, McShane L M, Dodd L, Gildersleeve J C. Profiling human serum antibodies with a carbohydrate antigen microarray. J Proteome Res. 2009; 8:4301-10.
34. Diaz S L, Padler-Karavani V, Ghaderi D et al. Sensitive and specific detection of the non-human sialic Acid N-glycolylneuraminic acid in human tissues and biotherapeutic products. PLoS ONE. 2009; 4:e4241.
35. Thompson I M, Ankerst D P, Chi C et al. Operating characteristics of prostate-specific antigen in men with an initial PSA level of 3.0 ng/ml or lower. JAMA. 2005; 294:66-70.
36. Cavadas V, Osorio L, Sabell F, Teves F, Branco F, Silva-Ramos M. Prostate Cancer Prevention Trial and European Randomized Study of Screening for Prostate Cancer Risk Calculators: A Performance Comparison in a Contemporary Screened Cohort. Eur Urol. 2010

37. Martin L T, Marth J D, Varki A, Varki N M. Genetically altered mice with different sialyltransferase deficiencies show tissue-specific alterations in sialylation and sialic acid 9-O-acetylation. J Biol. Chem. 2002; 277:32930-8.
38. Conze T, Carvalho A S, Landegren U et al. MUC2 mucin is a major carrier of the cancer-associated sialyl-Tn antigen in intestinal metaplasia and gastric carcinomas. Glycobiology. 2010; 20:199-206.
39. Yonezawa S, Tachikawa T, Shin S, Sato E. Sialosyl-Tn antigen. Its distribution in normal human tissues and expression in adenocarcinomas. Am J Clin Pathol. 1992; 98:167-74.
40. Cao Y, Stosiek P, Springer G F, Karsten U. Thomsen-Friedenreich-related carbohydrate antigens in normal adult human tissues: a systematic and comparative study. Histochem Cell Biol. 1996; 106:197-207.
41. Ogata S, Koganty R, Reddish M et al. Different modes of sialyl-Tn expression during malignant transformation of human colonic mucosa. Glycoconj J. 1998; 15:29-35.
42. Kobayashi H, Terao T, Kawashima Y. Serum sialyl Tn as an independent predictor of poor prognosis in patients with epithelial ovarian cancer. J Clin Oncol. 1992; 10:95-101.
43. Imai J, Ghazizadeh M, Naito Z, Asano G. Immunohistochemical expression of T, Tn and sialyl-Tn antigens and clinical outcome in human breast carcinoma. Anticancer Res. 2001; 21:1327-34.
44. Kim G E, Bae H I, Park H U et al. Aberrant expression of MUC5AC and MUC6 gastric mucins and sialyl Tn antigen in intraepithelial neoplasms of the pancreas. Gastroenterology. 2002; 123:1052-60.
45. Ju T, Cummings R D. A unique molecular chaperone Cosmc required for activity of the mammalian core 1 beta 3-galactosyltransferase. Proc Natl Acad. Sci. USA. 2002; 99:16613-8.
46. Ju T, Lanneau G S, Gautam T et al. Human tumor antigens Tn and sialyl Tn arise from mutations in Cosmc. Cancer Res. 2008; 68:1636-46.
47. Sewell R, Backstrom M, Dalziel M et al. The ST6GalNAc-I sialyltransferase localizes throughout the Golgi and Is responsible for the synthesis of the tumor-associated sialyl-Tn O-glycan in human breast cancer. J Biol. Chem. 2006; 281:3586-94.
48. Ostrand-Rosenberg S. Immune surveillance: a balance between protumor and antitumor immunity. Curr Opin Genet Dev. 2008; 18:11-8.
49. Slovin S F, Keding S J, Ragupathi G. Carbohydrate vaccines as immunotherapy for cancer. Immunol Cell Biol. 2005; 83:418-28.
50. de Leon J, Fernandez A, Clavell M et al. Differential influence of the tumour-specific non-human sialic acid containing GM3 ganglioside on CD4+CD25− effector and naturally occurring CD4+CD25+ regulatory T cells function. Int Immunol. 2008; 20:591-600.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiment, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A method for treating cancer in a subject, comprising
   a) obtaining a biological sample from the subject and applying said biological sample to a sialoglycan-microarray, said sialoglycan-microarray comprising at least four sialoglycan pairs, each of said at least four sialoglycan pairs differing only in the sialic acid residue present, wherein a first sialoglycan from each pair comprises Neu5Ac and a second sialoglycan from each pair comprises Neu5Gc, and wherein four sialoglycans of said at least 4 sialoglycan pairs comprise:
      i) N-glycolylneuraminic acid-alpha2-6-N-acetylgalactosamine-alpha-R (Neu5Gcα2-6GalNAcα-R),
      ii) Neu5Gc9Acα2-3Galβ1-4GlcNAcα-R,
      iii) Neu5Gcα2-6Lacβ-R, and
      iv) Neu5Gcα2-3Galβ1-3GalNAcβ-R,
   b) determining, in said biological sample, the level of one or more antibody, wherein said one or more antibody binds to at least one sialoglycan selected from the group consisting of:
      i) (Neu5Gcα2-6GalNAcα-R,
      ii) Neu5Gc9Acα2-3Galβ1-4GlcNAcα-R,
      iii) Neu5Gcα2-6Lacβ-R, and
      iv) Neu5Gcα2-3Galβ1-3GalNAcβ-R,
   c) comparing the level of said one or more antibody determined in step b) with the level of one or more antibody a control normal sample, wherein said one or more antibody in a control normal sample has the same binding specificity as said one or more antibody determined in step b),
   d) identifying said subject as having cancer when the level of said one or more antibody detected in step b) is higher relative to the level of said one or more antibody in a control normal sample, and
   e) initiating anti-cancer therapy in said subject identified as having cancer according to step d).

2. The method of claim 1, wherein said subject is a mammal.

3. The method of claim 2, wherein said subject is a human.

4. The method of claim 3, wherein said biological sample is selected from the group consisting of serum, saliva, cerebrospinal fluid (CSF) and tissue extract.

5. The method of claim 4, wherein said cancer comprises cancer of the prostate, ovary, lung, colon, pancreas, endometrium, parathyroid, thyroid, skin, breast or oropharynx.

6. The method of claim 1, wherein the sialoglycans on said sialoglycan-microarray comprise a non-reducing end linker group conjugated to a substrate.

7. The method of claim 6, wherein said substrate is selected from the group consisting of human serum albumin (HSA), a slide, a bead and an array.

8. The method of claim 1, comprising an additional step prior to step e), wherein said additional step comprises selecting said subject identified as having cancer according to step d) for initiation of anti-cancer therapy.

9. The method of claim 1, comprising an additional step prior to step e), wherein said additional step comprises selecting said subject identified as having cancer according to step d) for confirmatory diagnostic cancer testing.

10. The method of claim 1, further comprising performing a confirmatory diagnostic cancer test in a subject identified as having cancer according to step d).

11. The method of claim 1, wherein the one or more antibody detected in step b) has an area under the curve (AUC) for a Receiver Operator Characteristic (ROC) curve of cancer of greater than 0.50.

12. The method of claim 1, wherein said identifying according to step d) comprises a cancer specificity greater than 50% as calculated by the equation: specificity=number of true negatives/(number of true negatives+number of false positives).

13. The method of claim 1, wherein said identifying according to step d) comprises a cancer sensitivity greater than 50% as calculated by the equation: sensitivity=number of true positives/(number of true positives+number of false negatives).

\* \* \* \* \*